(12) United States Patent
Ding et al.

(10) Patent No.: US 8,962,772 B2
(45) Date of Patent: Feb. 24, 2015

(54) ANTIMICROBIAL SURFACE MODIFIED SILICONE RUBBER AND METHODS OF PREPARATION THEREOF

(71) Applicants: International Business Machines Corporation, Armonk, NY (US); Agency For Science, Technology and Research, Singapore (SG)

(72) Inventors: Xin Ding, Singapore (SG); James L. Hedrick, Pleasanton, CA (US); Chuan Yang, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 55 days.

(21) Appl. No.: 13/927,228

(22) Filed: Jun. 26, 2013

(65) Prior Publication Data
US 2015/0005457 A1    Jan. 1, 2015

(51) Int. Cl.
*C08F 283/00* (2006.01)
*C08G 77/388* (2006.01)
*A61F 5/44* (2006.01)
*C08J 7/02* (2006.01)
*C08J 7/06* (2006.01)
*C08F 283/02* (2006.01)

(52) U.S. Cl.
CPC ........... *C08G 77/388* (2013.01); *A61F 5/44* (2013.01); *C08J 7/02* (2013.01); *C08J 7/065* (2013.01)
USPC ........................................................ 525/461

(58) Field of Classification Search
USPC ........................................................ 525/461
See application file for complete search history.

(56) References Cited

U.S. PATENT DOCUMENTS

| 8,378,064 B2 | 2/2013 | Grinstaff et al. |
| 8,404,300 B2 | 3/2013 | Wang |
| 2002/0120333 A1 | 8/2002 | Keogh et al. |
| 2004/0132707 A1 | 7/2004 | Heinisch et al. |
| 2009/0123521 A1 | 5/2009 | Weber et al. |

OTHER PUBLICATIONS

Han, et al., "Immobilization of Amphiphilic Polycations by Catechol Functionality for Antimicrobial Coatings," Langmuir 2011, 27, 4010-4019; Published: Mar. 10, 2011.
Liu, et al., "Antimicrobial and Antifouling Hydrogels Formed in Situ from Polycarbonate and Poly(ethylene glycol) via Michael Addition," Adv. Mater. 2012, 24, 6484-6489.
Shalev, et al., "Non-leaching antimicrobial surfaces through polydopamine bio-inspired coating of quaternary ammonium salts or an ultrashort antimicrobial lipopeptide," J. Mater. Chem., 2012, 22, 2026-2032.
Yang, et al., "Stainless steel surfaces with thiol-terminated hyperbranched polymers for functionalization via thiol-based chemistry," Polym. Chem., 2013, 4, 3105-3115.
Ding, et al., "Antibacterial and antifouling catheter coatings using surface grafted PEG-b-cationic polycarbonate diblock copolymers," Biomaterials 33 (2012) 6593-6603; Available online Jun. 27, 2012.
Lee, et al., "Mussel-Inspired Surface Chemistry for Multifunctional Coatings," Science 318, (2007), 426-430. Available Oct. 19, 2007.

*Primary Examiner* — Terressa Boykin
(74) *Attorney, Agent, or Firm* — Michael R. Roberts

(57) ABSTRACT

An antimicrobial silicone rubber comprises a silicone rubber substrate, a catechol layer bound to a surface of the silicone rubber substrate, and an antimicrobial layer disposed on the catechol layer. The catechol layer comprises a catechol material, a quinone derivative thereof, and/or a polymer of the foregoing catechol material and/or quinone derivative. The antimicrobial layer comprises an antimicrobial cationic polycarbonate covalently linked to the catechol layer.

20 Claims, 17 Drawing Sheets

| Surfaces | Static Contact Angles | |
|---|---|---|
| Silicone Rubber | 106.3 ±3.2° |  |
| PDA Coating | 53.3° ±0.2° |  |
| P-1 Coating | 68.9° ±2.0° |  |
| P-2 Coating | 68.3 ±1.0° |  |
| P-3 Coating | 71° ±2.6° |  |

…

ANTIMICROBIAL SURFACE MODIFIED SILICONE RUBBER AND METHODS OF PREPARATION THEREOF

PARTIES TO A JOINT RESEARCH AGREEMENT

This invention was made under a joint research agreement between International Business Machines Corporation and the Agency For Science, Technology and Research.

BACKGROUND

The present invention relates to antimicrobial surface modified silicones and methods of preparation thereof, and more specifically, to silicone catheter materials having antimicrobial and antifouling surface layers.

Intravascular catheters, used mainly to administer fluids, medication, and to monitor hemodynamic status, have become indispensable for medical care in hospitals worldwide. However, these catheters are prone to bacterial adhesion and biofilm formation, which may result in subsequent bloodstream infection. Catheter-associated infections (CAIs) have become one of the most common sources of healthcare-associated infections. In the USA alone, more than 5 million central venous catheters are inserted each year and CAIs have been reported in up to 8% of inserted catheters, resulting in considerable morbidity and mortality. Additional financial costs attributable to CAIs can reach USD30,000 for each episode of infection, along with prolonged hospitalization. Biofilm formation on the catheters is the main cause for the CAIs. Once a mature biofilm is developed, the bacteria growing in the biofilm become highly resistant to both antimicrobial agents and host immune response. Coagulase-negative staphylococci are the most common causes of CAIs, followed by *Staphylococcus aureus* (*S. aureus*), including methicillin-resistant *S. aureus* (MRSA). The latter are more virulent and clinically important, with infections causing greater morbidity and mortality compared to coagulase-negative staphylococci.

Silicone rubber is an extensively used catheter material because of its flexibility, low toxicity and physiological inertness. However, microbes easily adhere to this material and cause infections. Several strategies to modify the silicone rubber surface to overcome this problem have been reported. For example, antibiotics (e.g., rifampin and minocycline) or silver have been coated onto catheter surfaces, and these surface coated catheters do prevent bacterial adhesion and biofilm formation. However, the risk of bacterial resistance and inadequate efficacy have hindered their clinical applications. In other strategies, polyacrylamide brushes and poly(ethylene oxide)-polypropylene oxide)-poly(ethylene oxide) triblock copolymer brushes were grafted onto the silicone rubber surface by polymerization from the silicone rubber surface in multiple steps. These modified silicone rubber surfaces successfully prevented the adhesion of *S. aureus*, *Streptococcus salivarius* (*S. salivarius*), *Staphylococcus epidermidis* (*S. epidermidis*) and *Candida albicans* (*C. albicans*). However, the complexity of growing polymer brushes from the rubber surface may lead to difficulty in characterization and batch-to-batch variation in coating thickness and quality.

In yet another strategy, thiol-terminated methoxy poly(ethylene glycol) (mPEG-SH) was grafted onto polydopamine coated substrates, and these modified surfaces exhibited antifouling property against mammalian cells for 2 days. Poly(ethylene glycol) (PEG) or PEG-based coatings have been of great interest in the drive to develop antifouling surfaces. However, decreased antifouling performance of PEG coating over time is a major drawback.

Therefore, a pressing need exists to develop a nontoxic, facile and effective catheter coating for the prevention of CAIs on silicone rubber materials.

SUMMARY

Accordingly, an antimicrobial silicone rubber is disclosed, comprising:
a silicone rubber substrate;
a catechol layer bound to a surface of the silicone rubber substrate, the catechol layer comprising a catechol material, a quinone derivative thereof, and/or a polymer of any of the foregoing; and
an antimicrobial layer disposed on the catechol layer, the antimicrobial layer comprising an antimicrobial cationic polycarbonate covalently linked to the catechol layer.

Also disclosed is a method, comprising:
treating a silicone rubber substrate with a first solution comprising a first solvent and a catechol material comprising a catechol group;
removing the first solvent, thereby forming a modified silicone rubber substrate comprising a catechol layer bound to a surface of the silicone rubber substrate, the catechol layer comprising the catechol material, a quinone derivative thereof, and/or a polymer of any of the foregoing;
treating the modified silicone rubber substrate with a second solution comprising a second solvent and a cationic polycarbonate comprising a nucleophilic group capable of reacting with the catechol layer to form a covalent bond; and
removing the second solvent, thereby forming an antimicrobial silicone rubber comprising an antimicrobial layer disposed on the catechol layer of the modified silicone rubber substrate, the antimicrobial layer comprising the antimicrobial cationic polycarbonate covalently bound to the catechol layer.

Also disclosed is an antimicrobial medical device, comprising:
a substrate;
a catechol layer bound to a surface of the substrate; and
an antimicrobial layer covalently bound to the catechol layer, wherein the antimicrobial layer is contacted by mammalian tissue and/or mammalian fluid during the intended use of the medical device;
wherein
the surface of the substrate comprises a material selected from the group consisting of metals, metal alloys, metal oxides, silicon oxides, semiconductors, ceramics, polymers, silicones, and combinations thereof,
the catechol layer comprises a catechol material, a quinone derivative thereof, and/or a polymer of any of the foregoing, and
the antimicrobial layer comprises an antimicrobial cationic polycarbonate.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 5A compares the uncoated silicone rubber, dopamine coated silicon rubber (labeled "PDA coating" for polydopamine) and dopamine+cationic polymer P-1 to P-3 (labeled "polymer 1 coating," "polymer 2 coating," and "polymer 3 coating," respectively). FIG. 5B is a high resolution spectrum of the N1s region for the dopamine coated silicon rubber. FIG. 5C is a high resolution spectrum of the N1s region for the dopamine+P-2 coated silicon rubber.

FIG. 15A is a magnified platelet image on the uncoated silicone rubber surface. Size of the scale bars: 10 micrometers.

DETAILED DESCRIPTION

Figure 1:
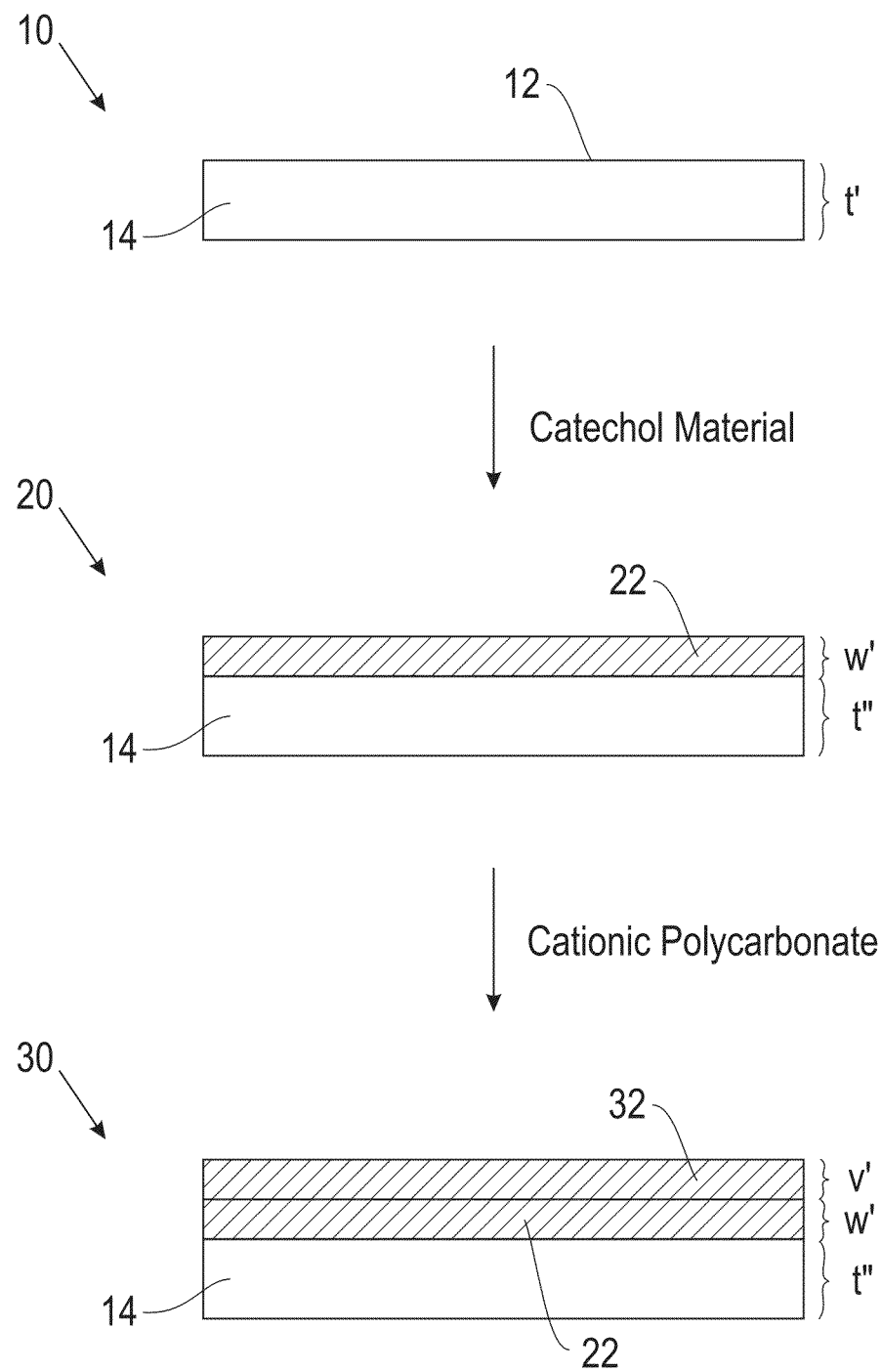
FIG. 1 is a series of cross-sectional layer diagrams illustrating a process of forming an antimicrobial silicone rubber.

Antimicrobial silicone rubber materials are disclosed comprising i) a silicone rubber substrate ii) a layer comprising a catechol material, referred to as a "catechol layer", bound to the silicone rubber substrate, and iii) a layer comprising an antimicrobial cationic polycarbonate, referred to herein as an "antimicrobial layer" bound to the catechol layer. The catechol layer can comprise the catechol material in the form of a catechol monomer, a polymer derivative of the catechol monomer, and/or a quinone derivative of any of the foregoing materials. The catechol material, polymer derivative thereof, and/or quinone derivative thereof can be bound to the silicone rubber substrate by covalent and/or non-covalent interactions. The cationic polycarbonate (also referred to as "cationic polymer") can be bound to the catechol layer by covalent and/or non-covalent interactions. In an embodiment, the cationic polymer is bound covalently to the catechol layer via a sulfur and/or amine linking group. The sulfur and/or amine linking group is preferably located at a terminal subunit of the cationic polycarbonate. Also disclosed are methods of preparing antimicrobial silicone rubber materials, and articles comprising antimicrobial silicone rubber materials.

Herein, silicone rubber materials are polymers consisting essentially of silicon, carbon, oxygen, and hydrogen. Each tetravalent silicon atom can be linked to m=1 to 4 oxygens and/or to n=0 to 3 carbons, wherein m+n=4. Thus, a silicone rubber can have a polymer backbone comprising subunits selected from the group consisting of Si(R')$_3$(O—*)$_1$, Si(R')$_2$(O—*)$_2$, Si(R')(O—*)$_3$, Si(O—*)$_4$, and combinations thereof, wherein each R' is an independent monovalent radical comprising at least one carbon, and the starred bonds represent attachment points to other subunits of the silicone rubber. In an embodiment, each R' is methyl. The silicone rubber materials can be crosslinked and/or branched polymers. In an embodiment, the silicone rubber material is a medical grade silicone rubber.

The catechol material comprises a catechol group:

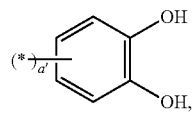

wherein a' is 0 to 4 and a starred bond represents an attachment point to another portion of the chemical structure. Preferably, the catechol material comprises a catechol group and a primary and/or secondary amine. Exemplary non-limiting catechol materials include catechol (a'=0), epinephrine, norepinephrine, dopamine, and L-dihydroxyphenylalanine.

The catechol material can be grafted onto a surface of the silicone rubber substrate by treating the silicone substrate with a first solution comprising the catechol material and a first solvent. In an embodiment, the first solvent is water, the first solution further comprises tris(hydroxymethyl)aminomethane (Tris), and the first solution has a pH of about 8.5. Tris is $(HOCH_2)_3CNH_2$ and has a pKa of 8.07. The treatment can be performed, for example, by immersing the silicone rubber substrate in the first solution, and heating the resulting mixture at about 50° C. for about 24 hours. The resulting modified silicone rubber substrate comprises a catechol layer disposed on a surface of the silicone rubber substrate, the catechol layer comprising a covalently or non-covalently bound form of the catechol material, polymeric derivatives thereof (e.g., polydopamine (PDA)), quinone derivatives of any of the foregoing, and/or Tris.

The cationic polycarbonate can be grafted onto the catechol layer of the modified silicone rubber substrate by immersing the modified silicone rubber substrate in a second solution comprising the cationic polymer and a second solvent. In an embodiment, the second solvent is water, the second solution comprises Tris, and the second solution has a pH of about 8.5. The treatment can be performed, for example, by immersing the treated silicone rubber substrate in the second solution, and heating the resulting mixture at about 50° C. for about 24 hours. The nucleophilic thiol groups and/or amine groups of the cationic polycarbonate can react with the catechol/quinone groups of the modified silicone rubber substrate via Michael addition and/or Schiff-base reactions to form covalent linkages to the catechol layer.

FIG. 1 is a series of cross-sectional layer diagrams illustrating an exemplary process of forming an antimicrobial silicone rubber. A silicone rubber substrate 10 comprising a surface 12 and silicone core 14 of thickness t' is treated with a first solution comprising a catechol material (e.g., dopamine) and a first solvent. Treatment of substrate 10 with the first solution can comprise, for example, immersing substrate 10 in the first solution for a period of time and at a temperature effective in grafting the catechol material to surface 12. Upon removal of the solvent, a modified silicone rubber substrate 20 is formed comprising catechol layer 22 of thickness w' and silicone core 14 of thickness t". Catechol layer 22 can comprise a covalently bound form of a catechol monomer, a polymeric derivative thereof, and/or a quinone derivative of any of the foregoing materials. Following this, the modified silicone rubber substrate 20 is treated with a second solution comprising a second solvent and a cationic polycarbonate comprising a terminal nucleophilic group selected from the group consisting of amines and thiols. This second sequential treatment comprises contacting catechol layer 22 with the second solution by, for example, immersing modified silicone rubber substrate 20 in the second solution for a period of time and at a temperature effective in grafting the cationic polycarbonate to catechol layer 22. Removing the second solvent results in an antimicrobial silicone rubber 30 comprising antimicrobial layer 32 of thickness v' disposed on catechol layer 22 of thickness w', which is disposed on silicone core 14 of thickness t". The thickness of antimicrobial layer 32, catechol layer 22, and silicone core 14 in the drawings are for clarity purposes, and not meant to depict relative scale. No restriction is placed on the thickness of antimicrobial layer 32 and/or the catechol layer 22 relative to the silicone core 14.

Catechol layer 22 and antimicrobial layer 32 are not necessarily sharply bounded layers. That is, intermixing can occur between catechol layer 22, the antimicrobial layer 32, and/or silicone core 14. Thus, the antimicrobial cationic polycarbonate and/or the catechol material can potentially be bound to the silicone core. In an embodiment, the total thickness (i.e., v'+w') of catechol layer 22 and antimicrobial layer 32 is about 5 nm to about 10 nm.

Figure 2:
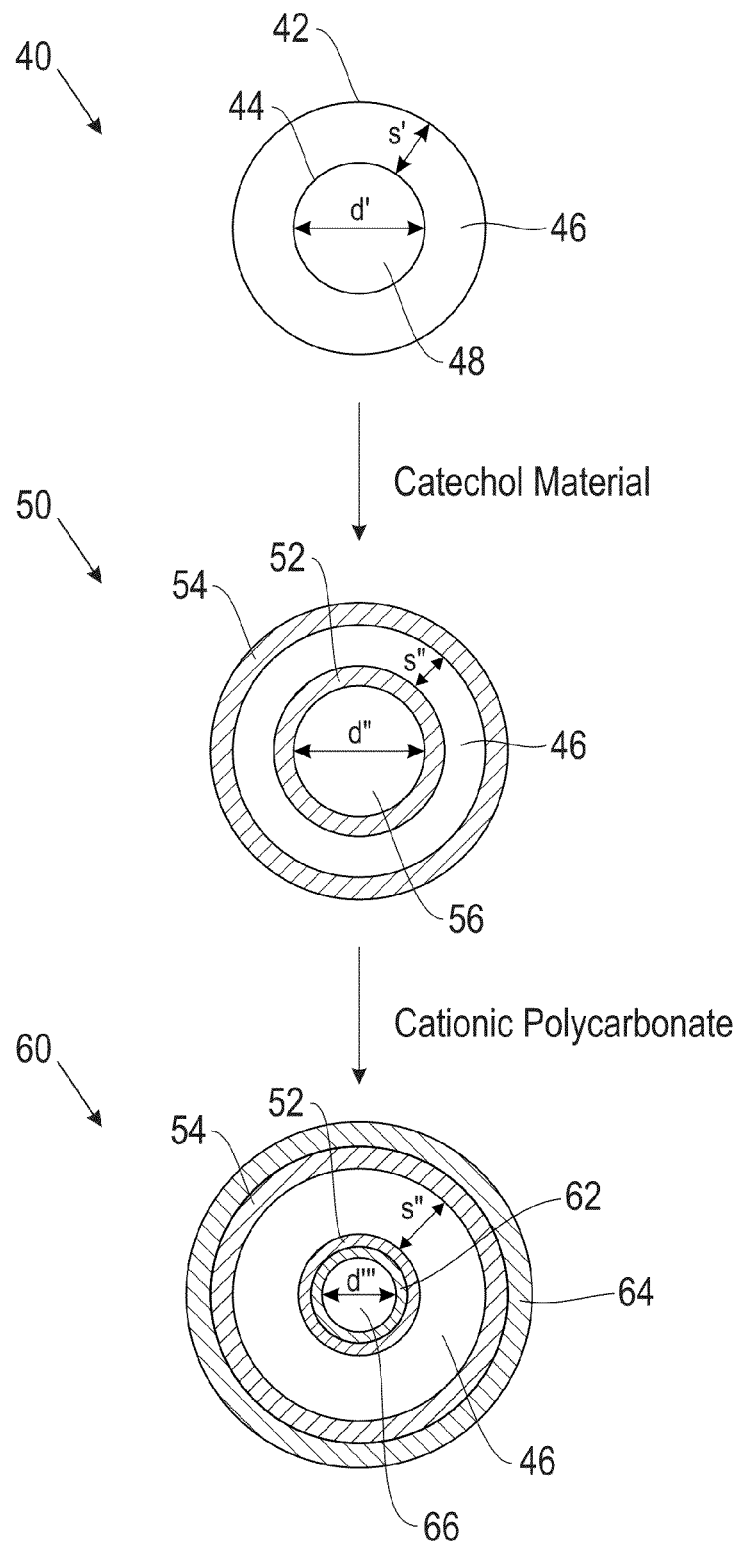
FIG. 2 is a series of cross-sectional layer diagrams illustrating a process of forming an antimicrobial silicone rubber tubing.

FIG. 2 illustrates the above-described process using a silicone rubber tubing 40 as the substrate. Silicon rubber tubing 40 comprises outer surface 42, inner surface 44, silicone core 46 of thickness s', and spatial region 48 having a diameter d'. Silicone rubber tubing 40 is treated with a first solution comprising a catechol material (e.g., dopamine) and a first solvent (e.g., using a process comprising an immersion step as described above). Removing the solvent results in a modified silicone rubber tubing 50 comprising a inner catechol layer 52 of thickness r' (not shown), outer catechol layer 54 of thickness r" (not shown), core 46 of thickness s", and spatial region 56 having inner diameter d". Following this, modified silicone rubber tubing 50 is treated with a second solution comprising a second solvent and a cationic polycarbonate, the cationic polycarbonate comprising a terminal nucleophilic group selected from the group consisting of amines and thiols (e.g., using a process comprising an immersion step as described above). Removing the second solvent results in antimicrobial silicone rubber tubing 60 comprising an antimicrobial inner layer 62 of thickness q' (not shown), antimicrobial outer layer 64 of thickness q" (not shown), inner catechol layer 52 of thickness r' (not shown), outer catechol layer 54 of thickness r" (not shown), silicone core 46 of thickness s", and spatial region 66 having inner diameter d'". The layers of modified silicone rubber tubing 50 and antimicrobial silicone rubber tubing 60 relative to silicone core 46 are drawn for clarity purposes and not to scale. In an embodiment, the value r'+q' equals about 5 nm to about 10 nm and r"+q" is about 5 nm to about 10 nm.

Intermixing can occur between catechol layer 54, antimicrobial layer 64, and/or silicone core 46.

Antimicrobial Cationic Polycarbonates

The cationic polymer can be a homopolymer, random copolymer, block copolymer, star polymer, or a mixture thereof. Preferably, the cationic polymer is a linear polymer, and more specifically, a linear polymer comprising one polycarbonate chain segment (one-armed cationic polymer) or two polycarbonate chain segments (two-armed cationic polymer. The cationic polymers comprise a nucleophilic group comprising an amine and/or thiol group capable of forming a covalent bond with the catechol layer. Preferably, the nucleophilic group is present in a polymer chain end group of the cationic polymer.

Several embodiments of antimicrobial cationic polymers follow.

Cationic Polymers Having One Polymer Chain (One-Armed)

The antimicrobial cationic polymers can have a structure in accordance with formula (1):

  (1), wherein

Z' is a monovalent first end group, wherein Z' comprises at least 1 carbon and a heteroatom selected from the group consisting of N, O, and S, wherein the heteroatom is linked to a backbone carbonyl group of P', Z" is a monovalent second end group selected from the group consisting of hydrogen and moieties comprising at least 1 carbon, Z' and/or Z" comprises a nucleophilic group selected from the group consisting of thiols, amines, and combinations thereof, which is capable of forming a covalent bond with a catechol, quinone, and/or a polymeric derivative any of the foregoing, P' is a polycarbonate chain consisting essentially of cationic carbonate repeat units, wherein i) P' has a degree of polymerization (DP) of about 5 to about 45, ii) each of the cationic carbonate repeat units comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group.

The first end group Z' can be any suitable end group comprising at least 1 carbon. In an embodiment, Z' is a residue of an initiator used in a ring opening polymerization to form the cationic polymer. Z' comprises an oxygen, nitrogen or sulfur heteroatom that is linked to a backbone carbonyl of P' in the form of a carbonate, carbamate or thiocarbonate group, respectively. In an embodiment, Z' is a polymer (e.g., poly (ethylene oxide) comprising a first end group linked to P' and a second end group comprising a nucleophilic thiol group and/or amine group capable of interacting with the catechol layer to form a covalent bond. In another embodiment, Z' is a non-polymeric $C_1$-$C_{45}$ fragment comprising a nucleophilic amine and/or thiol group (e.g., an oxyethylene thiol group having the structure *—OCH$_2$CH$_2$SH, wherein the oxygen is linked to P').

The initiator for the ring opening polymerization which becomes the residue Z' can comprise a nucleophilic group, or a protected form thereof during the ring opening polymerization, which in deprotected form is capable of reacting with the catechol layer to form a covalent bond.

The second end group Z" is preferably linked to a backbone oxygen of P'. When Z" is hydrogen, the cationic polymer has a terminal hydroxy group. When Z" is not hydrogen, Z" can be any suitable end group comprising at least 1 carbon. Z" can be polymeric or non-polymeric. In an embodiment, Z" is a covalently bound form of $C_1$-$C_{15}$ compound. In another embodiment, Z" is a fragment comprising a nucleophilic thiol group and/or amine group capable of interacting with the catechol layer to form a covalent bond.

In an embodiment, about 25% to about 100% of the cationic carbonate repeat units of formula (1), designated first cationic carbonate repeat units, have a cationic side chain comprising 13 to about 25 carbons, and about 0% to about 75% of the cationic carbonate repeat units, designated second cationic carbonate repeat units, have a cationic side chain comprising 6 to 12 carbons. The first cationic carbonate repeat units preferably comprise a cationic side chain having 13 to about 20 carbons, even more preferably 15 to about 20 carbons. In another embodiment, P' consists essentially of 25 mol % to about 75 mol % of the first cationic carbonate repeat units, and about 75 mol % to about 25 mol % of the second cationic carbonate repeat units. In another embodiment, P' consists essentially of 25 mol % to about 50 mol % of the first cationic carbonate repeat units, and about 75 mol % to about 25 mol % of the second cationic carbonate repeat units.

The cationic carbonate repeat units can have a structure according to formula (2):

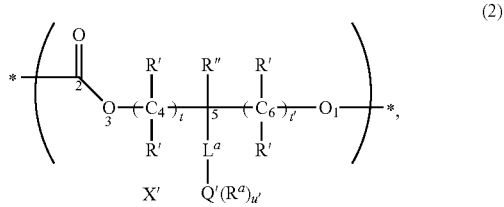

wherein $L^a$-$Q'(R^a)_{u'}$ is a $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2, t' is a positive integer having a value of 0 to 2, t and t' cannot both be zero, and X' is a negative-charged ion.

The starred bonds of formula (2) are attachment points to other portions of the polymer structure. The polymer backbone atoms of the cationic carbonate repeat unit are labeled 1 to 6 in formula (2). In this instance, the cationic side chain group is linked to backbone carbon 5 of the repeat unit. In an embodiment, t and t' are both 1, each R' is hydrogen, and R" is methyl or ethyl.

In a cationic polymer of formula (1) whose cationic carbonate repeat units are of formula (2), the first cationic carbonate repeat units have a cationic side chain $L^a$-$Q'(R^a)_{u'}$ comprising 13 to about 25 carbons. The second cationic carbonate repeat units have a cationic side chain $L^a$-$Q'(R^a)_{u'}$ comprising 6 to 12 carbons.

The cationic carbonate repeat units can have a structure in accordance with formula (3):

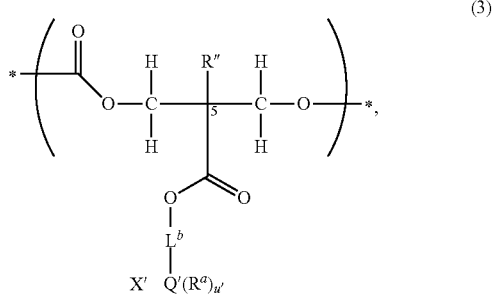

wherein $L^b$-$Q'(R^a)_{u'}$ is a $C_5$-$C_{24}$ cationic moiety comprising a quaternary ammonium group and/or quaternary phosphonium group, wherein $L^b$ is a divalent linking group comprising at least 2 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, R" is a monovalent radical selected from the group consisting of hydrogen, halogens, and alkyl groups comprising 1 to 6 carbons, and X' is a negative-charged ion.

In this instance, the cationic side chain group is $C(=O)O-L^b-Q'(R^a)_{u'}$ and $C(=O)O-L^b$ corresponds to divalent linking group $L^a$ of formula (2). The cationic side chain is linked to backbone carbon labeled 5.

In a cationic polymer of formula (1) whose cationic carbonate repeat units are of formula (3), the first cationic carbonate repeat units have a cationic side chain $C(=O)O-L^b-Q'(R^a)_{u'}$ comprising 13 to about 25 carbons. The second cationic carbonate repeat units have a cationic side chain $C(=O)O-L^b-Q'(R^a)_{u'}$ comprising 6 to 12 carbons.

The cationic repeat unit can have a structure in accordance with formula (4):

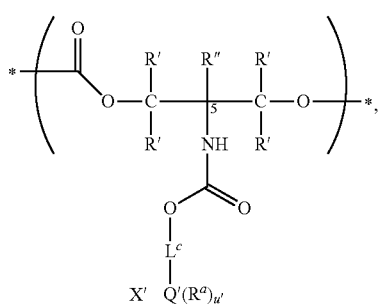

wherein $L^c-Q'(R^a)_{u'}$ is a $C_5-C_{24}$ cationic moiety comprising a quaternary ammonium group and/or quaternary phosphonium group, wherein $L^c$ is a divalent linking group comprising at least 2 carbons, Q' is a tetravalent positive-charged nitrogen or phosphorus, u' has a value of 1 to 3, and each $R^a$ is an independent radical having a valency of 1 to 3, wherein each $R^a$ comprises at least 1 carbon, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, and X' is a negative-charged ion.

In this instance the cationic side chain is $N(H)C(=O)O-L^c-Q'(R^a)_{u'}$ and $N(H)C(=O)O-L^c$ corresponds to divalent linking group $L^a$ of formula (2). The cationic side chain is linked to backbone carbon labeled 5. Serinol and/or threoninol provide useful starting materials for the formation of repeat units of formula (4).

In a cationic polymer of formula (1) whose cationic carbonate repeat units are of formula (4), the first cationic carbonate repeat units have a cationic side chain $N(H)C(=O)O-L^c-Q'(R^a)_{u'}$ comprising 13 to about 25 carbons. The second cationic carbonate repeat units have a cationic side chain $N(H)C(=O)O-L^c-Q'(R^a)_{u'}$ comprising 6 to 12 carbons.

Using the cationic repeat unit of formula (2), the cationic polymers of formula (1) can have a structure in accordance with formula (5):

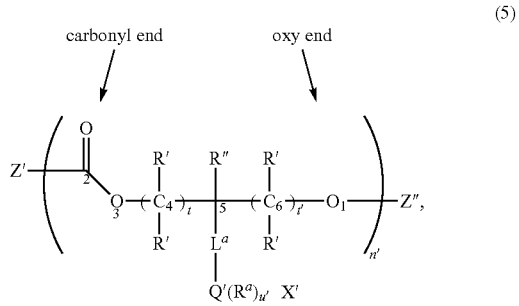

wherein:

n' represents the number of cationic carbonate repeat units, wherein n' has a value of about 5 to about 45, Z' is a monovalent first end group, wherein Z' comprises at least 1 carbon and a heteroatom selected from the group consisting of N, O, and S, wherein the heteroatom is linked to a backbone carbonyl group of the cationic polymer, Z" is a monovalent second end group selected from the group consisting of hydrogen and moieties comprising at least 1 carbon, Z' and/or Z" comprises a nucleophilic group selected from the group consisting of thiols, amines, and combinations thereof, which is capable of forming a covalent bond with a catechol, quinone, and/or a polymeric derivative of any of the foregoing, each $L^a-Q'(R^a)_{u'}$ is an independent $C_6-C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion.

As shown in formula (5), the polymer chain comprises a backbone portion comprising an oxycarbonyl group at a first end of the chain (referred to as the "carbonyl end"), and a backbone oxygen at a second end of the chain (referred to as the "oxy end"). The backbone atoms of the cationic carbonate repeat unit are shown numbered 1 to 6.

In an embodiment, about 25% to 100% of the cationic carbonate repeat units of the cationic polymer of formula (5), designated first cationic carbonate repeat units, have a cationic side chain $L^a-Q'(R^a)_{u'}$ comprising 13 to about 25 carbons, and 0% to about 75% of the cationic carbonate repeat units of the cationic polymer, designated second cationic carbonate repeat units, have a cationic side chain $L^a-Q'(R^a)_{u'}$ comprising 6 to 12 carbons. In formula (5), $L^a$ and $Q'(R^a)_{u'}$ of the first cationic carbonate repeat units can individually have 3 to about 22 carbons, with the proviso that $L^a-Q'(R^a)_{u'}$ has a total of 13 to about 25 carbons. Preferably, the $L^a$ group of the first cationic carbonate repeat units comprises 5 to about 12 carbons, or more preferably 8 to about 12 carbons. Preferably, $Q'(R^a)_{u'}$ of the first cationic carbonate repeat units comprise 3 to about 18 carbons, more preferably 4 to about 18 carbons. Likewise, $L^a$ and $Q'(R^a)_{u'}$ of the second cationic carbonate repeat units of formula (5) can each have at least 3 carbons, with the proviso that $L^a$-$Q'(R^a)_{u'}$ has a total of 6 to 12 carbons.

In an embodiment, Z" is hydrogen. In another embodiment, the first cationic carbonate repeat units have a cationic side chain $L^a$-$Q'(R^a)_{u'}$ comprising 15 to about 20 carbons.

The antimicrobial cationic polymer can be a random copolymer having a structure in accordance with formula (6):

$$Z'—P'''—Z'' \quad (6),$$

wherein

Z' is a monovalent first end group, wherein Z' comprises at least 1 carbon and a heteroatom selected from the group consisting of N, O, and S, wherein the heteroatom is linked to a backbone carbonyl group of P''', Z" is a monovalent second end group selected from the group consisting of hydrogen and moieties comprising at least 1 carbon, Z' and/or Z" comprises a nucleophilic group selected from the group consisting of thiols, amines, and combinations thereof, which is capable of forming a covalent bond with a catechol, quinone, and/or a polymeric derivative of any of the foregoing, P''' is a random polymer chain consisting essentially of I) about 40 mol % to 70 mol % of cationic carbonate repeat units, and II) 60 mol % to about 30 mol % of hydrophobic non-charged carbonate repeat units, wherein i) P''' has a degree of polymerization (DP) of about 5 to about 45, ii) each of the cationic carbonate repeat units comprises a polymer backbone portion and a cationic side chain portion linked to the polymer backbone portion, and iii) each cationic side chain portion comprises a positively charged heteroatom of a quaternary ammonium group and/or a quaternary phosphonium group.

In an embodiment, about 25% to 100% of the cationic carbonate repeat units of the cationic polymer of formula (6), designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons. $L^a$ and $Q'(R^a)_{u'}$ of the first cationic carbonate repeat units of formula (6) can individually have 3 to about 22 carbons, with the proviso that $L^a$-$Q'(R^a)_{u'}$ has a total of 10 to about 25 carbons. In an embodiment, the first cationic carbonate repeat units of formula (6) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

The antimicrobial cationic polymers of formula (6) can have a structure in accordance with formula (7):

wherein n' represents the number of cationic carbonate repeat units, wherein n' has a value greater than 0, m' represents the number of carbonate repeat units, wherein m' has a value greater than 0, n'+m' has a value of about 5 to about 45, a ratio of m':n' is about 30:70 to about 60:40, Z' is a monovalent first end group, wherein Z' comprises at least 1 carbon and a heteroatom selected from the group consisting of N, O, and S, wherein the heteroatom is linked to a backbone carbonyl group of the cationic polymer, Z" is a monovalent second end group selected from the group consisting of hydrogen and moieties comprising at least 1 carbon, Z' and/or Z" comprises a nucleophilic group selected from the group consisting of thiols, amines, and combinations thereof, which is capable of forming a covalent bond with a catechol, quinone, and/or a polymeric derivative of any of the foregoing, each $L^d$ is an independent divalent linking group selected from the group consisting of single bond and monovalent radicals comprising 1 to about 10 carbons, each H' is an independent non-charged monovalent radical comprising at least 1 carbon, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion.

The vertical stacking of repeat units within the square brackets of formula (7) indicates a random distribution of repeat units within the polymer chain.

In an embodiment, about 25% to 100% of the cationic carbonate repeat units of the cationic polymer of formula (7), designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons. $L^a$ and $Q'(R^a)_{u'}$ of the first cationic carbonate repeat units of formula (7) can individually have 3 to about 22 carbons, with the proviso that $L^a$-$Q'(R^a)_{u'}$ has a total of 10 to about 25 carbons. In an embodiment, the first cationic carbonate repeat units of formula (7) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

The discussion that follows applies to all disclosed cationic polymer structures herein.

Exemplary non-limiting divalent $L^a$ groups include:

-continued

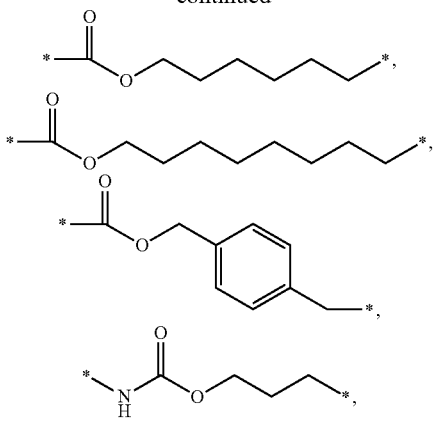

and combinations thereof. In these examples, the starred bonds of the carbonyl and carbamate nitrogen are linked to the polycarbonate backbone (e.g., the backbone carbon labeled 5 in the above cationic carbonate repeat units), and the starred bonds of the methylene groups are linked to Q'.

Together, $L^a$ and $Q'(R^a)_{u'}$ form a quaternary ammonium group or a quaternary phosphonium group, meaning the positive-charged heteroatom Q' is bonded to a carbon of $L^a$ and up to three independent $R^a$ groups.

Each $R^a$ comprises at least one carbon. Each $R^a$ can be a monovalent hydrocarbon substituent (e.g., methyl, ethyl, etc.), in which case u' is 3.

An $R^a$ can form a ring with Q', in which case the $R^a$ of the ring has a valency of 2. For example, $Q'(R^a)_{u'}$ can be:

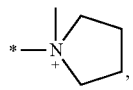

wherein the starred bond is linked to $L^a$, Q' is nitrogen, and u' is 2. In this example, a first $R^a$ is a divalent butylene group ($*$—$(CH_2)_4$—$*$), and a second $R^a$ is methyl.

$R^a$ can form a multi-cyclic moiety with Q'. For example $Q'(R^a)_{u'}$ can be:

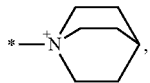

wherein the starred bond is linked to $L^a$, Q' is nitrogen, u' is 1, and $R^a$ is the fragment

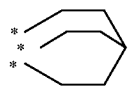

having a valency of 3.

The $R^a$ groups can also independently comprise oxygen, nitrogen, sulfur, and/or another heteroatom. In an embodiment, each $R^a$ is an independent monovalent branched or unbranched hydrocarbon substituent.

Exemplary non-limiting $R^a$ groups include methyl, ethyl, n-propyl, iso-propyl, n-butyl, iso-butyl, n-pentyl, n-hexyl, n-heptyl, n-octyl, and benzyl. The $R^a$ groups can be used in combination.

Exemplary non-limiting $Q'(R^a)_{u'}$ groups include:

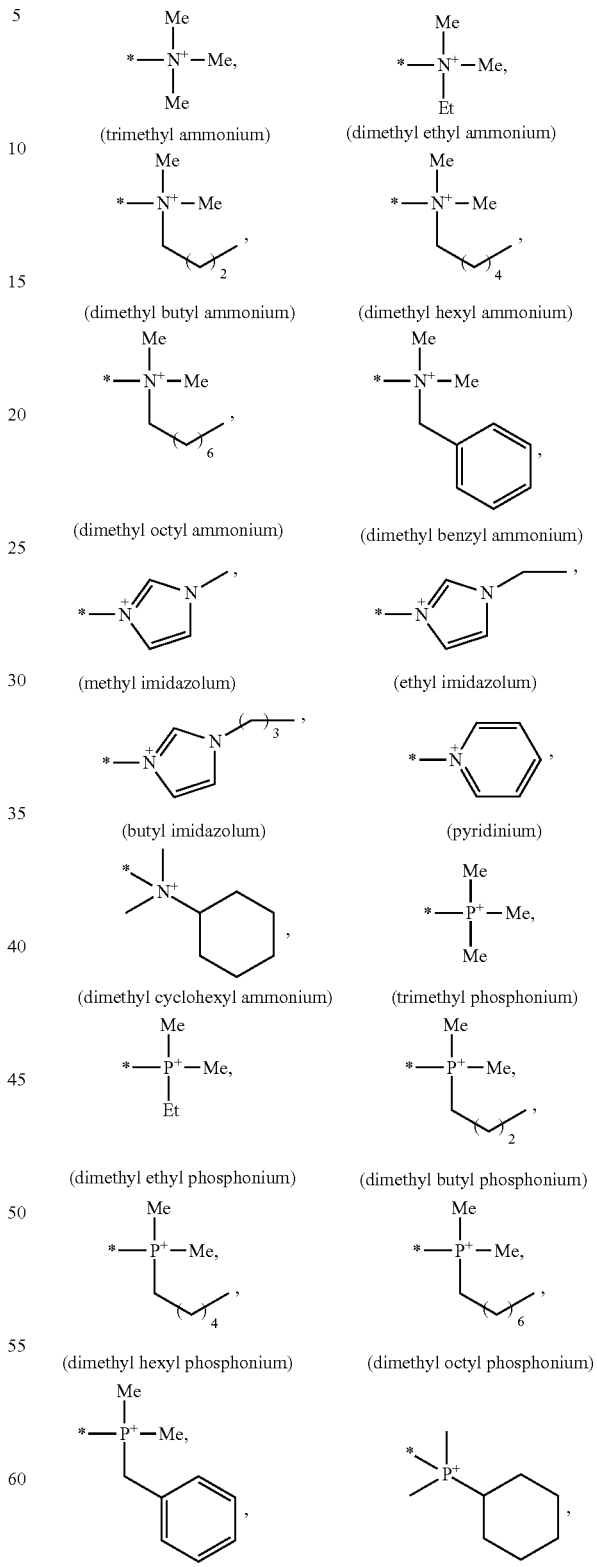

and combinations thereof.

In the foregoing examples, it should be understood that the positive-charged nitrogen and phosphorus are tetravalent, and the starred bond is linked to a carbon of $L^a$. The Q' groups can be present in the cationic polymer singularly or in combination.

Exemplary negative-charged ions X' include halides (e.g., chloride, bromide, and iodide), carboxylates (e.g., acetate and benzoate), and/or sulfonates (e.g., tosylate). The X' ions can be present singularly or in combination.

Exemplary non-limiting cationic carbonate repeat units include the following:

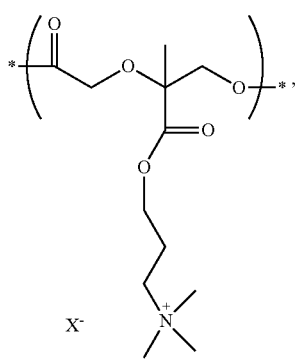

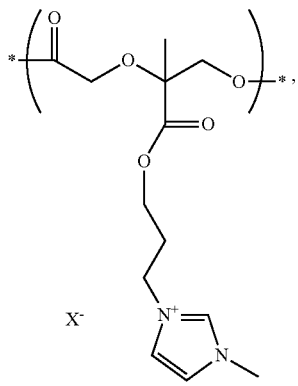

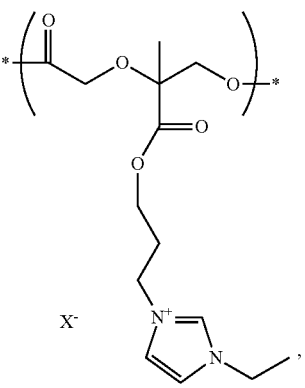

-continued

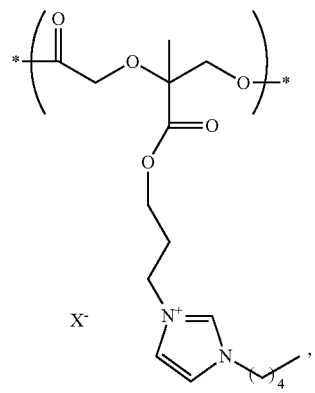

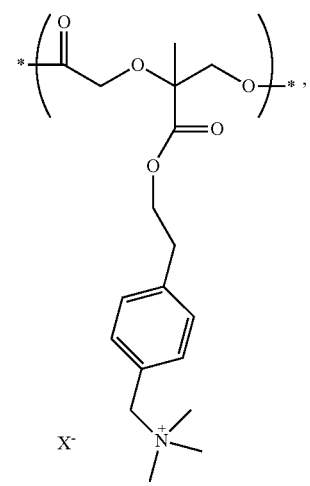

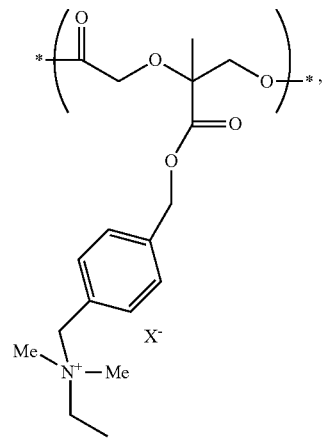

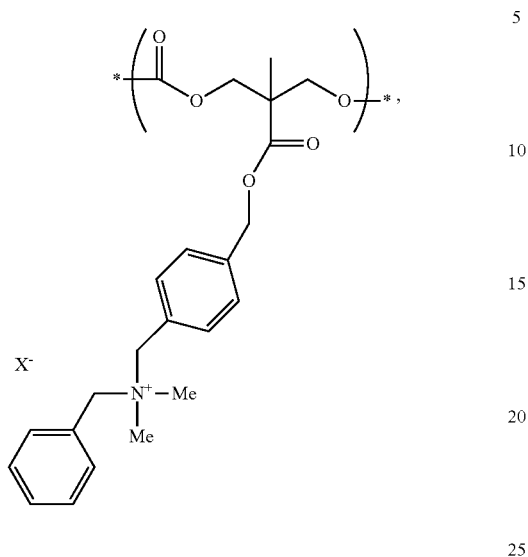
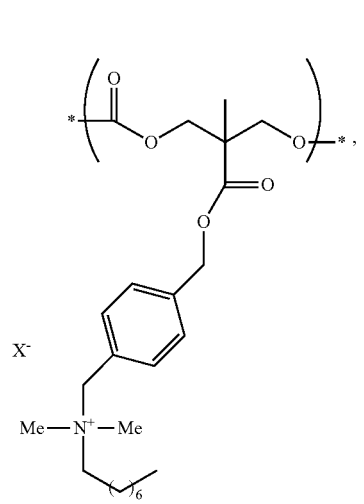
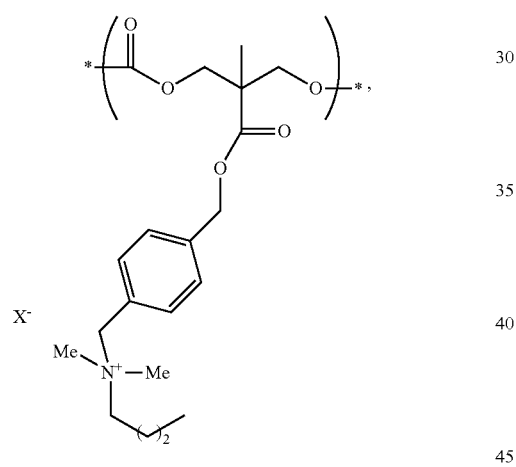
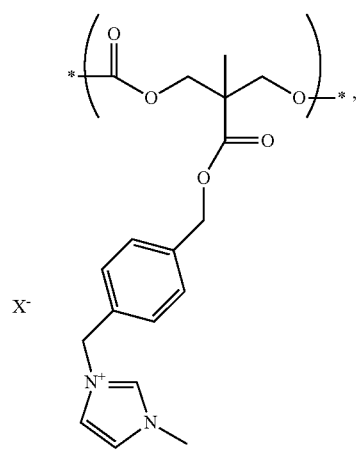
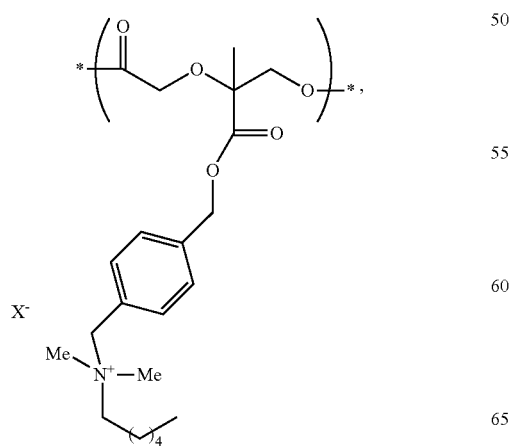
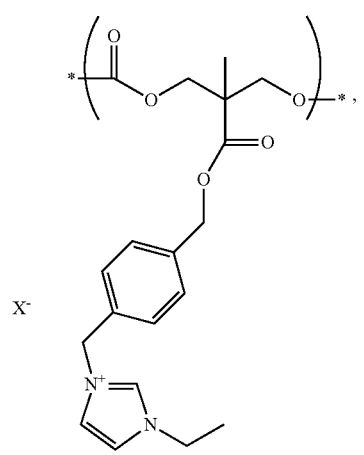

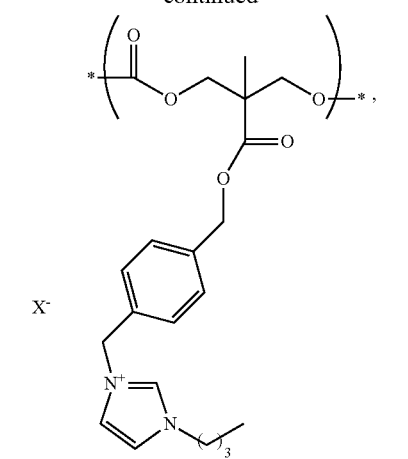
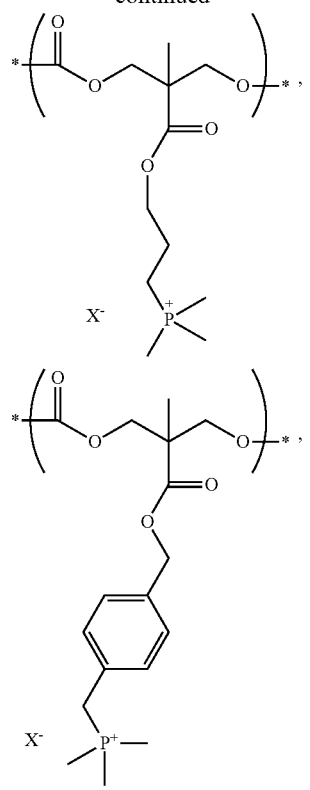
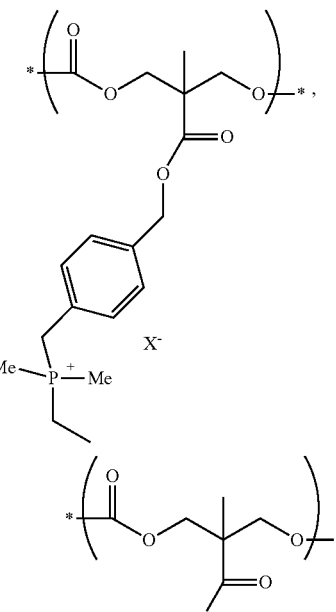
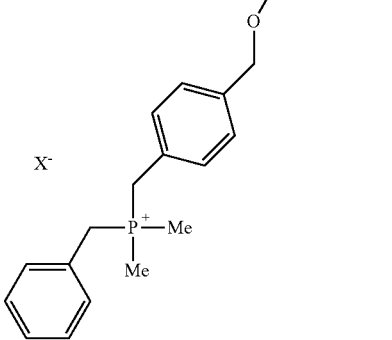

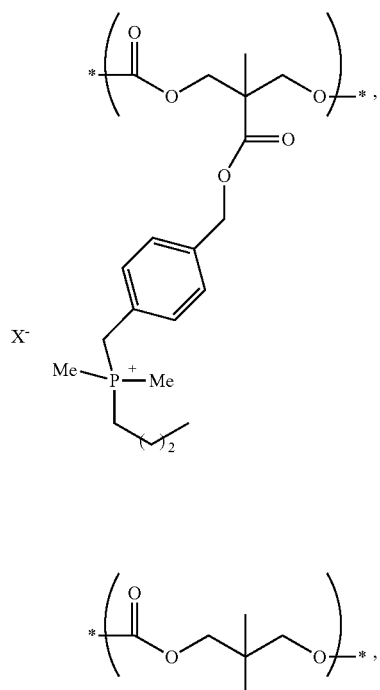

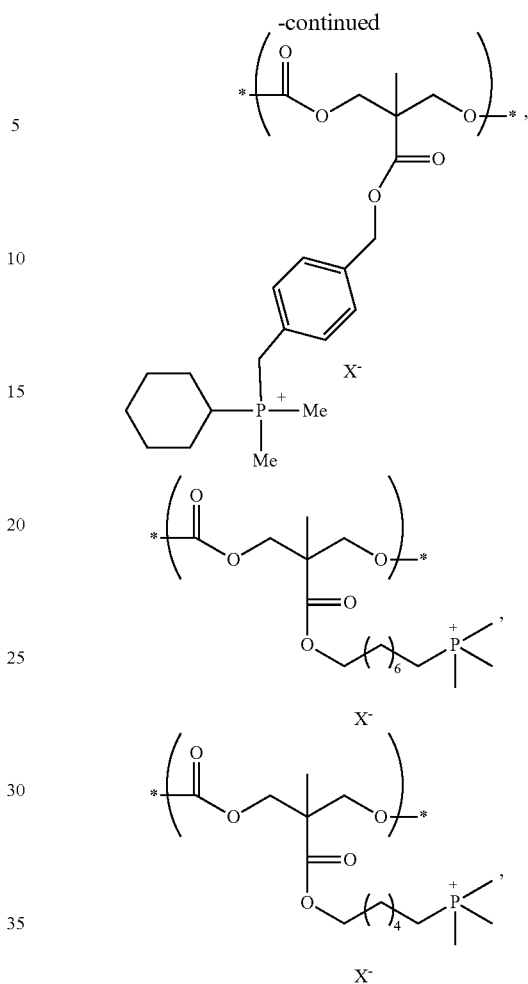

and combinations thereof, wherein X⁻ is a negative-charged ion.

In general, antimicrobial activity of the cationic polymers is favored by spacing the positive-charged heteroatom Q' from the polycarbonate backbone in 25 mol % to 100 mol % of the cationic carbonate repeat units (first cationic carbonate repeat units) by the shortest path having 6 or more contiguously linked atomic centers from the polymer backbone. The shortest path is defined as the lowest number of contiguously linked atomic centers joining Q' to the polymer backbone. The contiguously linked atomic centers should be understood to be between the polycarbonate backbone and Q'. For example, if $L^a$-Q' is:

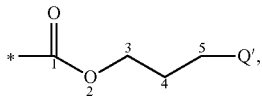

then the shortest path from the polymer backbone to Q' has 5 contiguously linked atomic centers, as numbered. The shortest path does not include the carbonyl oxygen. As another example, if $L^a$-Q' is

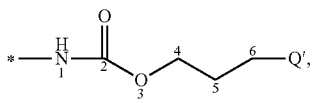

then the shortest path from the polymer backbone to Q' has 6 contiguously linked atomic centers, as numbered. The shortest path does not include the amide hydrogen and the carbonyl oxygen. As another example, if $L^a$-$Q'$ is

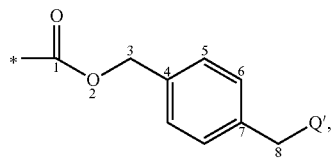

then the shortest path from the polymer backbone to $Q'$ has 8 contiguously linked atomic centers, as numbered. The shortest path does not include two carbons of the aromatic ring and the carbonyl oxygen. As another example, if $L^a$-$Q'$ is

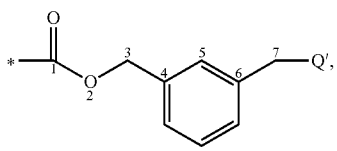

then the shortest path from the polymer backbone to $Q'$ has 7 contiguously linked atomic centers, as numbered. The shortest path does not include three carbons of the aromatic ring and the carbonyl oxygen. Finally, as another example, if $L^a$-$Q'$ is

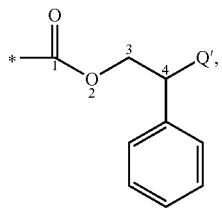

then the shortest path from the polymer backbone to $Q'$ has 4 contiguously linked atomic centers, as numbered. The shortest path does not include the aromatic ring and the carbonyl oxygen.

Preferably, $Q'$ of the first carbonate repeat units is spaced from the polymer backbone by a shortest path having 6 to about 18 contiguously linked atomic centers, and more preferably 8 to about 15 contiguously linked atomic centers.

Cationic Polymers Having Two Cationic Polymer Chains (Two-Armed Cationic Polymers)

The antimicrobial cationic polymers can have a structure in accordance with formula (8):

wherein $C'$ is a $C_2$-$C_{15}$ divalent linking group joining polymer chains $P^b$, wherein $C'$ comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, $Z^c$ is an independent monovalent end group selected from the group consisting of hydrogen and moieties comprising at least 1 carbon, $Z^d$ is an independent monovalent end group selected from the group consisting of hydrogen and moieties comprising at least 1 carbon, $Z^c$, $Z^d$ and/or $C'$ comprises a nucleophilic group selected from the group consisting of thiols, amines, combinations thereof, and protected forms thereof, which in a non-protected form is capable of forming a covalent bond with the catechol layer, each polymer chain $P^b$ is a polycarbonate consisting essentially of cationic carbonate repeat units, wherein i) the cationic polymer comprises a total of 5 to about 45 cationic carbonate repeat units, ii) each of the cationic carbonate repeat units comprises a backbone portion of the polymer chain and a cationic side chain linked to the backbone portion, and iii) the cationic side chain comprises a positive-charged heteroatom $Q'$ of a quaternary ammonium group and/or quaternary phosphonium group.

In an embodiment, about 25% to 100% of all the cationic carbonate repeat units of the cationic polymer of formula (8), designated first cationic carbonate repeat units, have a cationic side chain comprising 10 to about 25 carbons, and 0% to about 75% of the cationic carbonate repeat units of the cationic polymer, designated second cationic carbonate repeat units, have a cationic side chain comprising 6 to 9 carbons. $L^a$ and $Q'(R^a)_{u'}$ of the first cationic carbonate repeat units of formula (8) can individually have 3 to about 22 carbons, with the proviso that $L^a$-$Q'(R^a)_{u'}$ has a total of 10 to about 25 carbons. In an embodiment, the first cationic carbonate repeat units of formula (8) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

$C'$ can be a residue of an initiator that comprises two initiating sites for ring opening polymerization. The initiator can further comprise a nucleophilic group, or a protected form thereof, which in deprotected form can react with the catechol layer to form a covalent bond. The initiator can comprise the nucleophilic group in a protected form during the ring opening polymerization, after which the protected nucleophilic group is deprotected for reaction with the catechol layer. In an embodiment, $Z^c$ and $Z^d$ are hydrogen, and $C'$ comprises a nucleophilic group selected from the group consisting of thiols, amines, combinations thereof, and protected forms thereof, which is capable in a non-protected form of reacting with the catechol layer to form a covalent bond.

In another embodiment, the positive-charged heteroatom $Q'$ of the first cationic carbonate repeat units is spaced from the backbone portion by a shortest path having 6 to about 15 contiguously linked atomic centers between $Q'$ and the backbone portion.

More specific cationic polymers of formula (8) have a structure according to formula (9):

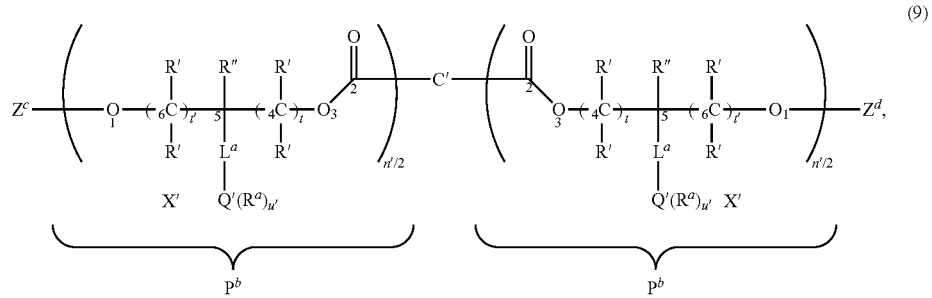

(9)

wherein
n' represents the total number of cationic carbonate repeat units of the cationic polymer, and has a value of about 5 to about 45, C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, the polymer chains $P^b$ consist essentially of the cationic carbonate repeat units, $Z^c$ is an independent monovalent end group selected from the group consisting of hydrogen and moieties comprising at least 1 carbon, $Z^d$ is an independent monovalent end group selected from the group consisting of hydrogen and moieties comprising at least 1 carbon, $Z^c$, $Z^d$ and/or C' comprises a nucleophilic group selected from the group consisting of thiols, amines, combinations thereof, and protected forms thereof, which in a non-protected form is capable of forming a covalent bond with the catechol layer, each $L^a$-$Q'(R^a)_{u'}$ is an independent $C_6$-$C_{25}$ cationic side chain comprising a quaternary ammonium group and/or quaternary phosphonium group, wherein La is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R'' is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and
each X' is an independent negative-charged ion.

In an embodiment, about 25% to 100% of the cationic carbonate repeat units of the cationic polymer of formula (9), designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons. $L^a$ and $Q'(R^a)_{u'}$ of the first cationic carbonate repeat units of formula (9) can individually have 3 to about 22 carbons, with the proviso that $L^a$-$Q'(R^a)_{u'}$ has a total of 10 to about 25 carbons. In an embodiment, the first cationic carbonate repeat units of formula (9) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

The antimicrobial cationic polymers can have a structure in accordance with formula (10):

$$Z^c-P^c-C'-P^c-Z^d \qquad (10),$$

wherein
C' is a $C_2$-$C_{15}$ divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, $Z^c$ is an independent monovalent end group selected from the group consisting of hydrogen and moieties comprising at least 1 carbon, $Z^d$ is an independent monovalent end group selected from the group consisting of hydrogen and moieties comprising at least 1 carbon, $Z^c$, $Z^d$ and/or C' comprises a nucleophilic group selected from the group consisting of thiols, amines, combinations thereof, and protected forms thereof, which in a non-protected form is capable of forming a covalent bond with the catechol layer, each $P^c$ is a polymer chain consisting essentially of I) about 40 mol % to 70 mol % of cationic carbonate repeat units, and II) 60 mol % to about 30 mol % of a hydrophobic non-charged carbonate repeat unit, wherein i) the cationic polymer has a total number of repeat units of about 5 to about 45, ii) each of the cationic carbonate repeat units comprises a polymer backbone portion and a $C_6$-$C_{25}$ cationic side chain portion linked to the polymer backbone portion, and iii) each cationic side chain portion comprises a positive-charged heteroatom Q' of a quaternary ammonium group and/or quaternary phosphonium group.

In an embodiment, about 25% to 100% of the cationic carbonate repeat units of the cationic polymer of formula (10), designated first cationic carbonate repeat units, have a cationic side chain group comprising 10 to about 25 carbons, and 0% to about 75% of the cationic carbonate repeat units of the cationic polymer, designated second cationic carbonate repeat units, have a cationic side chain group comprising 6 to 9 carbons. $L^a$ and $Q'(R^a)_{u'}$ of the first cationic carbonate repeat units of formula (10) can individually have 3 to about 22 carbons, with the proviso that $L^a$-$Q'(R^a)_{u'}$ has a total of 10 to about 25 carbons. In an embodiment, the first cationic carbonate repeat units of formula (10) have a cationic side chain comprising 13 to about 25 carbons, and the second cationic carbonate repeat units have a cationic side chain comprising 6 to 12 carbons.

The cationic polymers of formula (10) can have a structure according to formula (11):

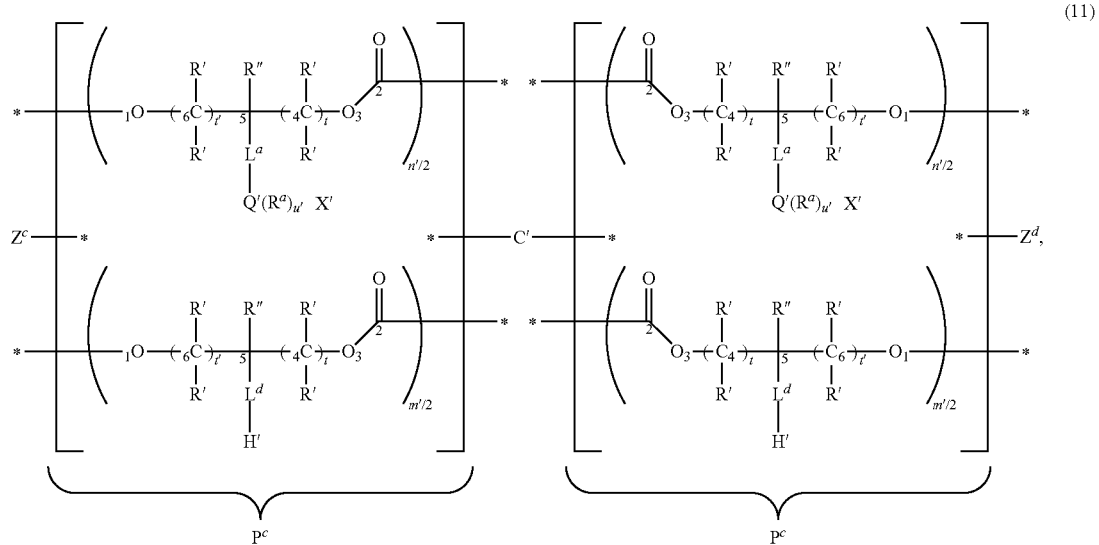

wherein n' represents the total number of cationic carbonate repeat units, wherein n' has a value greater than 0, m' represents the total number of carbonate repeat units, wherein m' has a value greater than 0, n'+m' has a value of about 5 to about 45, and a ratio m':n' is about 30:70 to about 60:40, C' is a $C_2$-$C_{15}$ non-polymeric divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, $Z^c$ is an independent monovalent end group selected from the group consisting of hydrogen and moieties comprising at least 1 carbon, $Z^d$ is an independent monovalent end group selected from the group consisting of hydrogen and moieties comprising at least 1 carbon, $Z^c$, $Z^d$ and/or C' comprises a nucleophilic group selected from the group consisting of thiols, amines, combinations thereof, and protected forms thereof, which in a non-protected form is capable of forming a covalent bond with the catechol layer, each $L^d$ is an independent divalent linking group selected from the group consisting of single bond and monovalent radicals comprising 1 to about 10 carbons, each H' is an independent monovalent radical comprising a non-charged hydrophobic group comprising at least 1 carbon each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion.

In an embodiment about 25% to 100% of the cationic carbonate repeat units of the cationic polymer of formula (11), designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons. $L^a$ and $Q'(R^a)_{u'}$ of the first cationic carbonate repeat units of formula (11) can individually have 3 to about 22 carbons, with the proviso that $L^a$-$Q'(R^a)_{u'}$ has a total of 10 to about 25 carbons. In an embodiment, the first cationic carbonate repeat units of formula (11) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

Non-limiting exemplary H' groups include methyl, ethyl, propyl, butyl, and phenyl.

Cation-Forming Cyclic Carbonate Monomers

A preferred method of preparing the disclosed cationic polymers utilizes a cyclic carbonate monomer capable of forming a cationic moiety before or after the polymerization. These are referred to as cation-forming monomers, which have the formula (12):

(12)

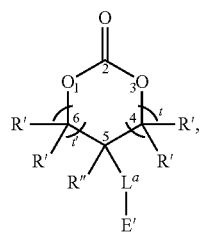

wherein
the ring atoms are shown numbered 1 to 6,
$L^a$ is a divalent linking group comprising at least 3 carbons,
E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons,
each R' is an independent monovalent radical selected from the group consisting of hydrogen, halogens, methyl, and ethyl,
R" is a monovalent radical selected from the group consisting of hydrogen, halogens, and alkyl groups comprising 1 to 6 carbons,
t is a positive integer having a value of 0 to 2,
t' is a positive integer having a value of 0 to 2, and
t and t' cannot both be zero.

The cation-forming monomers of formula (12) have a ring substituent $L^a$-E'. This ring substituent $L^a$-E' becomes a side chain of the initial polymer formed by the ring opening polymerization of the cation-forming monomer. E' can be an electrophilic and/or nucleophilic group so long as the side chain $L^a$-E' is capable of reacting to produce a $C_6$-$C_{25}$ cationic side chain $L^a$-$Q'(R^a)_{u'}$ of the cationic polymer. Preferably, E' is a leaving group capable of reacting with a tertiary amine to form a quaternary ammonium group, and/or reacting with a tertiary phosphine to form a quaternary phosphonium group.

The cation-forming monomers can be stereospecific or non-stereospecific.

In an embodiment, t and t' of formula (12) are each 1, each R' at carbon 4 is hydrogen, each R' at carbon 6 is hydrogen, and R" at carbon 5 is selected from the group consisting of hydrogen, methyl, and ethyl.

Ring opening polymerization of cation-forming monomers of formula (12) produces an initial polycarbonate having a repeat unit according to formula (13):

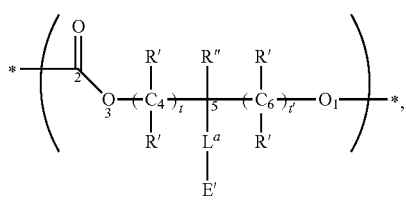

wherein
backbone atoms are shown numbered 1 to 6,
$L^a$ is a divalent linking group comprising at least 3 carbons,
E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3,
each $R^a$ is an independent radical having a valency of 1 to 3, wherein each $R^a$ comprises at least 1 carbon, and together $Q'(R^a)_{u'}$ and $L^a$ comprise 6 to about 25 carbons,
each R' is an independent monovalent radical selected from the group consisting of hydrogen, halogens, methyl, and ethyl,
R" is a monovalent radical selected from the group consisting of hydrogen, halogens, and alkyl groups comprising 1 to 6 carbons,
t is a positive integer having a value of 0 to 2,
t' is a positive integer having a value of 0 to 2, and
t and t' cannot both be zero.

More specific cation-forming monomers have the formula (14):

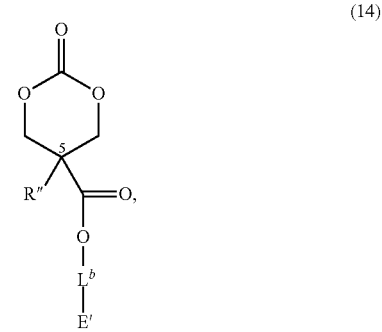

wherein
ring atom 5 is labeled,
$L^b$ is a divalent linking group comprising at least 2 carbons,
E' is a substituent capable of reacting to produce a cationic moiety $Q'(R^a)_{u'}$ linked to $L^b$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^b$ comprise 5 to about 24 carbons, and
R" is a monovalent radical selected from the group consisting of hydrogen, halogens, and alkyl groups comprising 1 to 6 carbons.

Ring opening polymerization of cation-forming monomers of formula (14) produces a polycarbonate having a repeat unit according to formula (15):

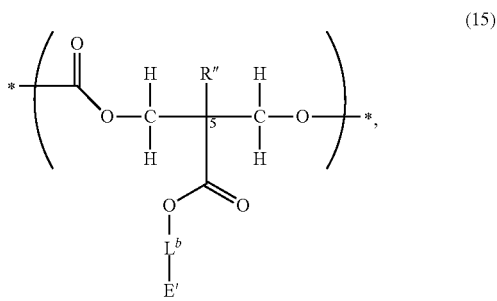

wherein
backbone atom 5 is labeled,
$L^b$ is a divalent linking group comprising at least 2 carbons,
E' is a substituent capable of reacting to produce a cationic moiety $Q'(R^a)_{u'}$ linked to $L^b$, wherein Q' is a tetravalent positive-charged nitrogen or phosphorus, u' has a value of 1 to 3,
each $R^a$ is an independent radical having a valency of 1 to 3, wherein each $R^a$ comprises at least 1 carbon, and together $Q'(R^a)_{u'}$ and $L^b$ comprise 5 to about 24 carbons, and R" is a monovalent radical selected from the group consisting of hydrogen, halogens, and alkyl groups comprising 1 to 6 carbons.

The cation-forming monomers can have the formula (16):

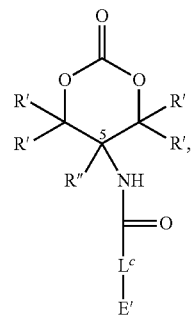

(16)

wherein
ring atom 5 is labeled,
$L^c$ is a divalent linking group comprising at least 2 carbons,
E' is a substituent capable of reacting to produce a cationic moiety $Q'(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

Ring opening polymerization of cation-forming monomers of formula (16) produces an initial polycarbonate having a repeat unit according to formula (17):

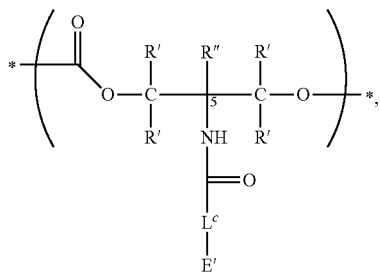

(17)

wherein
backbone atom 5 is labeled,
$L^c$ is a divalent linking group comprising at least 2 carbons,
E' is a substituent capable of reacting to produce a cationic moiety $Q'(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons,
each R' is an independent monovalent radical selected from the group consisting of hydrogen, halogens, methyl, and ethyl, and R" is a monovalent radical selected from the group consisting of hydrogen, halogens, and alkyl groups comprising 1 to 6 carbons.

Exemplary cation-forming monomers include the cyclic carbonate monomers of Table 1.

TABLE 1

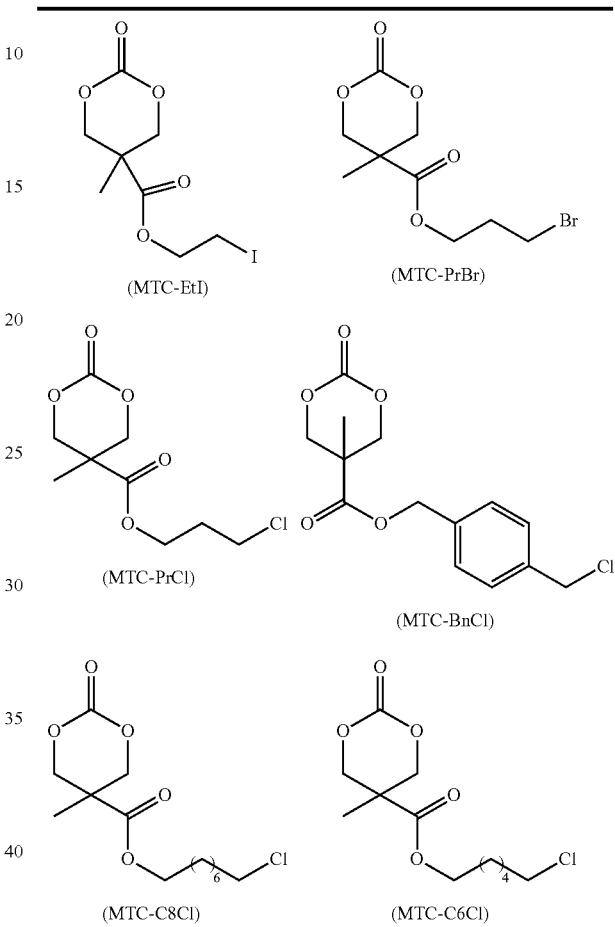

Mononucleophilic Initiators for One-Armed Cationic Polymers

Nucleophilic initiators for ROP generally include alcohols, amines, and/or thiols.

ROP initiators capable of forming ring opened polymers having one polymer chain (one-armed ROP polymers) are mono-nucleophilic initiators. (e.g., ethanol, n-butanol, benzyl alcohol, and the like). Herein, a mono-nucleophilic initiator can include more than one nucleophilic group (e.g., thioethanol), but only one nucleophilic group of the initiator initiates the ROP under the conditions used to perform the polymerization.

ROP initiators capable of forming ring opened polymers having two polymer chains (two-armed ROP polymers) are di-nucleophilic initiators. Herein, a di-nucleophilic initiator can include more than two nucleophilic groups (e.g., 2-mercapto-1,3-propanediol), but only two nucleophilic groups of the initiator initiate the ROP under the conditions used to perform the polymerization. Exemplary di-nucleophilic ROP initiators include ethylene glycol, butanediol, 1,4-benzenedimethanol, and Bn-MPA:

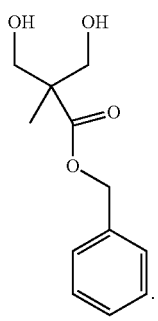 [SMILES: CC(CO)(CO)C(=O)OCc1ccccc1]

Preferably, the ROP initiator used in the formation of the disclosed cationic polycarbonate comprises one or two primary alcohol groups for initiating ROP and one or more thiol groups that do not participate as initiators in the ROP under the reaction conditions employed for the ring opening polymerization. Non-limiting examples of these initiators include the non-polymeric thioalcohol initiators described above and polymeric thioalcohol initiators such as, for example, HS-PEG-OH, a polyethylene oxide in which one end group is OH and a second end group is SH:

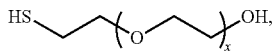

wherein x has a value of about 50 to about 150, and more specifically 100 to about 120. Under the conditions used for the ROP, HS-PEG-OH is a mono-nucleophilic initiator. That is, chain growth occurs substantially or exclusively at the hydroxy end, forming a block copolymer having a thiol terminated poly(ethylene oxide) block and a polycarbonate block having a terminal alcohol group.

The ROP initiator can be used singularly or in combination with a different ROP initiator. The ROP initiator can be stereospecific or non-stereospecific.

ROP Polymerization

Using a cyclic carbonate monomer of formula (12) to illustrate a method of making the disclosed cationic polymers, a reaction mixture is formed which comprises a cyclic carbonate monomer of formula (12), a catalyst, an optional accelerator, a mono-nucleophilic ROP initiator (optionally comprising a thiol group that does not participate in the ROP), and a solvent. Agitating the reaction mixture forms an initial polymer. Optionally the initial polymer can be endcapped to form an endcapped initial polymer. The resulting polymer has a structure according to formula (18):

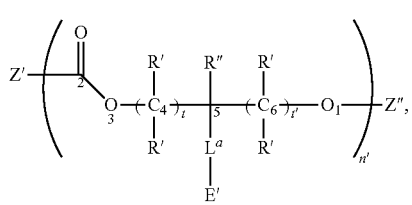

wherein n' represents the number of cationic carbonate repeat units, wherein n' has a value of about 5 to about 45, Z' is a monovalent first end group comprising 1 or more carbons and a heteroatom selected from the group consisting of N, O, and S, wherein the heteroatom is linked to a backbone carbonyl group of the cationic polymer, Z'' is a monovalent second end group selected from the group consisting of hydrogen and groups comprising 1 or more carbons, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons, each R' is an independent monovalent radical selected from the group consisting of hydrogen, halogens, methyl, and ethyl, each R'' is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, and no carbonate repeat unit has t=0 and t'=0.

In this instance, each carbonate repeat unit of the initial polymer comprises a side chain E' group.

Z' can be a residue of the ROP initiator. In an embodiment, Z' comprises an oxy residue of the initiating group linked to a backbone carbonyl and a thiol group for binding to the catechol layer.

The living end (oxy end) of the initial polymer formed by the ROP has a reactive hydroxy group (second end group Z''=H), which is capable of initiating another ROP. The living end can be treated with an endcap agent, thereby forming a second end group (Z'' contains at least one carbon), which is capable of preventing further chain growth and stabilizing the polymer against unwanted side reactions such as chain scission. The polymerization and endcapping can occur in the same pot without isolating the initial polymer. Endcap agents include, for example, materials for converting terminal hydroxy groups to esters, such as carboxylic acid anhydrides, carboxylic acid chlorides, and reactive esters (e.g., p-nitrophenyl esters). In an embodiment, the endcap agent is an acylating agent, and the second end group Z'' is an acyl group. In another embodiment the acylating agent is acetic anhydride, and the second end group Z'' is an acetyl group. In another embodiment, Z'' comprises a thiol group.

The initial polymer and/or the endcapped initial polymer can be treated chemically, thermally, and/or photochemically to convert E' to a positive-charged $Q'(R^a)_{u'}$ group, thereby forming a cationic polymer. For example, E' can be an electrophilic leaving group (e.g., chloride, bromide, iodide, sulfonate ester, and the like), which is capable of undergoing a nucleophilic displacement reaction with a Lewis base (e.g., tertiary amine, trialkyl phosphine) to form a quaternary ammonium group and/or a phosphonium group. In an embodiment, E' is chloride, bromide, and/or iodide. In another embodiment, the cyclic carbonate monomer is a compound of formula (14) and the initial polymer comprises a repeat unit of formula (15). In another embodiment, the cyclic carbonate monomer is a compound of formula (16) and the initial polymer comprises a repeat unit of formula (17).

Also contemplated is a method of forming the cationic polymer using a cationic cyclic carbonate monomer that comprises a positive-charged Q' group. In this instance, the ROP forms an initial cationic polymer having a living end unit (i.e., a nucleophilic hydroxy end group capable of initiating a subsequent ROP). The living end unit can be endcapped to prevent unwanted side reactions and/or to introduce a nucleophilic group capable of forming a covalent bond with the catechol layer.

Exemplary non-limiting tertiary amines for forming quaternary amines by a nucleophilic substitution reaction with electrophilic E' groups include trimethylamine, triethylamine, tri-n-propylamine, tri-iso-propylamine, tri-n-butylamine, tri-n-pentylamine, dimethylethylamine, dimethylpropylamine, dimethyl-iso-propylamine, dimethylbutylamine, dimethylpentylamine, dimethylbenzylamine, diethylmethylamine, diethylpentylamine, diethylbutylamine, N,N-dimethylcyclohexylamine, N-methylimidazole, N-ethylimidazole, N-(n-propyl)imidazole, N-isopropylimidazole, N-(n-butyl)imidazole, N,N-diethylcyclohexylamine, N,N-dimethylaniline, N,N-diethylaniline, pyridine, and combinations thereof.

Exemplary non-limiting tertiary phosphines for forming quaternary phosphonium groups by a nucleophilic substitution reaction with electrophilic E' groups include trimethylphosphine, triethylphosphine, tripropylphosphine, tributylphosphine, ethyldimethylphosphine, propyldimethylphosphine, butyldimethylphosphine, pentyldimethylphosphine, hexyldimethylphosphine, heptyldimethylphosphine, octyldimethylphosphine, methyldiethylphosphine, propyldiethylphosphine, butyldiethylphosphine, pentyldiethylphosphine, hexyldiethylphosphine, heptyldiethylphosphine, octyldiethylphosphine, pentyldipropylphosphine, pentyldibutylphosphine, dipentylmethylphosphine, dipentylethylphosphine, dipentylpropylphosphine, dipentylbutylphosphine, tripentylphosphine, hexyldipropylphosphine, hexyldibutylphosphine, cyclohexyl-dimethylphosphine, cyclohexyldiethylphosphine, dihexylmethylphosphine, dihexyl-ethylphosphine, dihexylpropylphosphine, benzyldimethylphosphine, and combinations thereof.

The ring-opening polymerization can be performed at a temperature that is about ambient temperature or higher, more specifically 15° C. to 200° C., and even more specifically 20° C. to 80° C. Preferably, the ROP is performed at ambient temperature. Reaction times vary with solvent, temperature, agitation rate, pressure, and equipment, but in general the polymerizations are complete within 1 to 100 hours.

The ROP reaction is preferably performed with a solvent. Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerization is conducted under an inert dry atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

Preferably, the chemical formula of the catalyst used for the ring opening polymerization does not include an ionic or nonionic form of a metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferred catalysts are organocatalysts whose chemical formulas contain none of the above metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

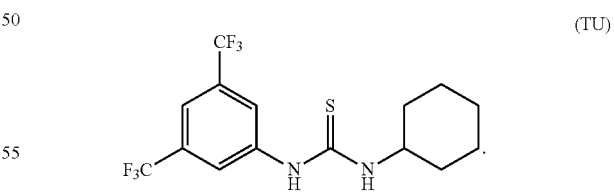

Other ROP organocatalysts comprise at least one 1,1,1,3,3,3-hexafluoropropan-2-ol-2-yl (HFP) group. Singly-donating hydrogen bond catalysts have the formula (19):

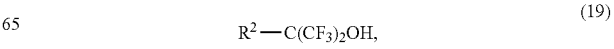

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 2.

TABLE 2

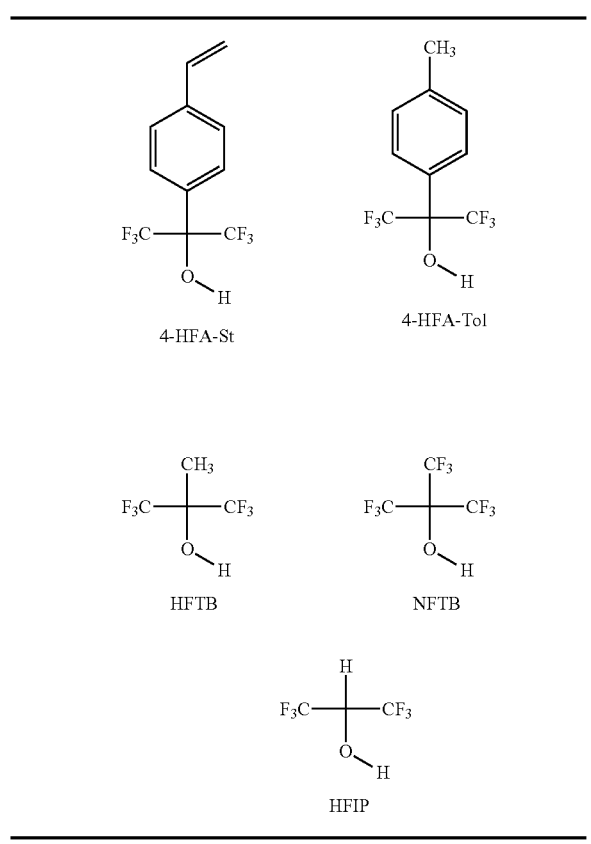

Doubly-donating hydrogen bonding catalysts have two HFP groups, represented by the formula (20):

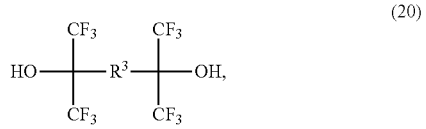

(20)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (20) include those listed in Table 3. In a specific embodiment, $R^2$ is an arylene or substituted arylene group, and the HFP groups occupy positions meta to each other on the aromatic ring.

TABLE 3

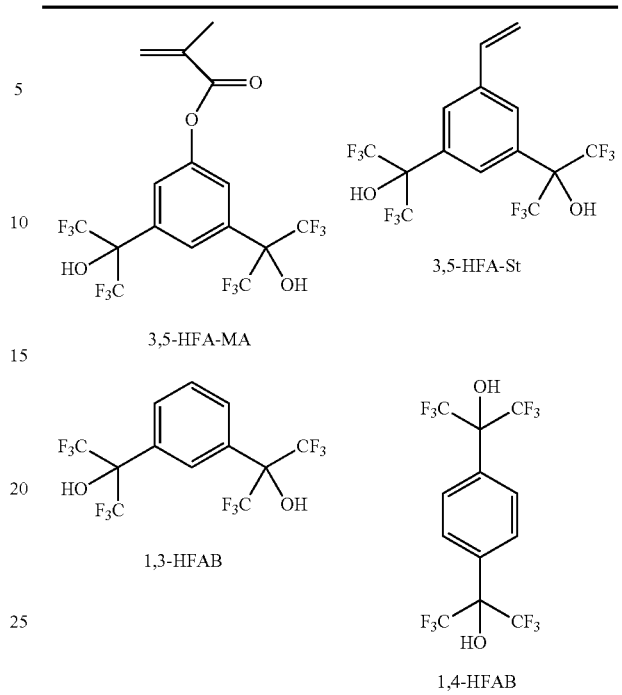

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]

dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl)imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 4.

TABLE 4

Pyridine (Py)

N,N-Dimethyl-aminocyclohexane (Me₂NCy)

4-N,N-Dimethyl-aminopyridine (DMAP)

trans 1,2-Bis(dimethyl-amino)cyclohexane (TMCHD)

1,8-Diaza-bicyclo[5.4.0]undec-7-ene (DBU)

7-Methyl-1,5,7-trizabicyclo[4.4.0]dec-5-ene (MTBD)

1,5,7-Triaza-bicyclo[4.4.0]dec-5-ene (TBD)

(−)-Sparteine (Sp)

1,3-Bis(2-propyl)-4,5-dimethylimidazol-2-ylidene (Im-1)

TABLE 4-continued 1,3-Bis(2,4,6-trimethylphenyl)imidazol-2-ylidene (Im-2)

1,3-Bis(2,6-di-i-propylphenyl)imidazol-2-ylidene (Im-3)

1,3-Bis(1-adamantyl)imidazol-2-yliden (Im-4)

1,3-Di-i-propylimidazol-2-ylidene (Im-5)

1,3-Di-t-butylimidazol-2-ylidene (Im-6)

1,3-Bis(2,4,6-trimethylphenyl)-4,5-dihydroimidazol-2-ylidene (Im-7)

1,3-Bis(2,6-di-i-propylphenyl)-4,5-dihydroimidazol-2-ylidene (Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The initiator groups are preferably present in an amount of 0.001 to 10.0 mol %, 0.1 to 2.5 mol %, 0.1 to 1.0 mol %, or 0.2 to 0.5 mol %, based on total moles of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on total moles of cyclic carbonate monomer.

The catalysts can be removed by selective precipitation or, in the case of the solid supported catalysts, by filtration. The catalyst can be present in an amount of 0 wt % (weight percent) to about 20 wt %, preferably 0 wt % (weight percent) to about 0.5 wt % based on the total weight of the cationic polymer and the residual catalyst. The cationic polymer preferably comprises no residual catalyst.

Average Molecular Weight.

The cationic polymers have a number average molecular weight (Mn) as determined by size exclusion chromatography of about 1500 to about 50,000, more specifically about 1500 to about 30,000. The precursor polymer to the cationic polymer and/or the cationic polymer preferably has a polydispersity index (PDI) of 1.01 to about 1.5, more particularly 1.01 to 1.30, and even more particularly 1.01 to 1.25.

More specific cationic polymers comprise i) a first block of poly(ethylene glycol) (PEG) terminated with a thiol and/or a nucleophilic primary and/or secondary amine, and ii) a second block comprising a cationic polycarbonate chain that includes a carbonate repeat unit comprising a side chain comprising a positive-charged group (e.g., quaternary amine). The polycarbonate chain can comprise one or more hydrophobic carbonate repeat units.

The cationic polymer is preferably formed by an organocatalyzed ring opening polymerization of a cyclic carbonate monomer having a pendant group capable of reacting with a tertiary amine and/or tertiary phosphine after the polymerization, thereby forming carbonate repeat units comprising a quaternary amine group and/or a quaternary phosphonium group, respectively. The ring opening polymerization is preferably initiated by an initiator having an alcohol group for initiating the ROP, and a thiol group for reaction with the catechol layer (e.g., 2-thioethanol and/or the polymer HS-PEG-OH). The alcohol group of the HS-PEG-OH can initiate the ring opening polymerization in the presence of the thiol group, forming a precursor polymer for quaternization. The quaternization of the precursor polymer can also be performed in the presence of the thiol group. The thiol group serves to anchor the cationic polymer to the silicone rubber surface.

In some instances the cationic polymers can self-assemble into nanoparticulate micelles in de-ionized water. The cationic polymers can have a critical micelle concentration (CMC) of about 15 mg/L to about 45 mg/L.

The high antimicrobial activity and low cytotoxicity of these cationic polymers makes these cationic polymers highly attractive for forming antimicrobial films disposed on medically useful substrates such as silicone rubber.

Also disclosed is a medical device comprising the disclosed antimicrobial silicone rubber. Exemplary medical devices include catheters.

Also disclosed is a method of treating a microbe, comprising contacting a microbe with a disclosed antimicrobial silicone rubber, thereby killing the microbe. Non-limiting microbes include Gram-positive *Staphylococcus epidermidis* (*S. epidermidis*), Gram-positive *Staphylococcus aureus* (*S. aureus*), Gram-negative *Escherichia coli* (*E. coli*), Gram-negative *Pseudomonas aeruginosa* (*P. aeruginosa*), Gram-positive fungus *Candida albicans* (*C. albicans*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), Gram-positive yeast *Cryptococcus neoformans* (*C. neoformans*), and Gram-negative *Klebsiella pneumoniae* (*K. pneumoniae*).

Also disclosed are antimicrobial medical devices comprising substrates other than silicone. These devices can comprise i) a substrate composed of a material selected from the group consisting of metals (e.g., titanium), metal alloys (e.g., stainless steel), metal oxides, silicon oxides, semiconductors, ceramics, polymers, silicones and combinations thereof, ii) a catechol layer comprising a catechol material, a quinone derivative thereof, and/or a polymer of any of the foregoing bound to a surface of the substrate, and iii) an antimicrobial layer comprising an antimicrobial cationic polymer covalently bound to the catechol layer, which contacts mammalian tissue and/or mammalian fluids during the intended use of the medical device. Exemplary polymers include but are not limited to polystyrenes, polyethylenes, polycarbonates, poly(ethylene terephthalate), polyetheretherketones, polyurethanes, and combinations thereof.

The following examples illustrate the formation and use of antimicrobial silicone rubber materials.

EXAMPLES

Materials used in the following examples are listed in Table 5.

TABLE 5

| ABBREVIATION | DESCRIPTION | SUPPLIER |
|---|---|---|
| DBU | 1,8-Diazabicyclo[5,4,0]undec-7-enep-Chloromethyl Benzyl Alcohol | Sigma-Aldrich Sigma-Aldrich |
| TMA | Trimethylamine | Sigma-Aldrich |
| DCM | Dichloromethane | Sigma-Aldrich |
| TU | N-Bis(3,5-Trifluoromethyl)Phenyl-N'-Cyclohexylthiourea | Prepared as described below |
| BnOH | Benzyl Alcohol, initiator for ROP | Sigma-Aldrich |
| 4-MeBnOH | 4-Methyl Benzyl Alcohol, initiator for ROP | Sigma-Aldrich |
| HS-PEG-OH | Poly(ethylene oxide) terminated with by thiol and alcohol groups; Mn 5000 g/mol, PDI 1.03 | RAPP Polymere GmbH |
| MPEG | Monomethyl Endcapped Poly(ethylene glycol) terminated with by thiol and alcohol groups; Mn 5000 g/mol, PDI 1.05 | RAPP Polymere GmbH |

Herein, Mn is the number average molecular weight, Mw is the weight average molecular weight, and MW is the molecular weight of one molecule.

HS-PEG-OH (Mn 5000 g/mol, PDI 1.03) and CH$_3$O-PEG-OH (also called MPEG, Mn 5000 g/mol, PDI 1.05) were purchased from RAPP Polymere GmbH (Germany), which was freeze-dried and transferred to a glove-box at least one day prior to use. 1,8-Diazabicyclo[5,4,0]undec-7-ene (DBU) was stirred over CaH$_2$ and vacuum distilled before being transferred to a glove-box. All other chemical reagents such as dopamine hydrochloride and bovine serum albumin (BSA) were bought from Sigma-Aldrich and used as received unless otherwise mentioned. Silicone kit SYLGARD 184 was purchased from Dow Corning and used according to the suggested protocols. A LIVE/DEAD Baclight bacterial viability kit (L-7012) was purchased from Invitrogen. A commercial strain of S. aureus (ATCC No. 6538) was bought from ATCC (U.S.A). Two clinical MRSA isolates belonging to ST239-III and ST22-IV were obtained from a local hospital.

N-bis(3,5-trifluoromethyl)phenyl-N'-cyclohexylthiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH$_2$, filtering, and removing solvent under vacuum.

Monomer Synthesis

Cyclic carbonate monomers can be prepared from 2,2-bis(methylol)propionic acid (bis-MPA) using the route shown in Scheme 1.

This approach parallels that of (meth)acrylate derivatization and has been demonstrated to create a wide selection of functional monomers capable of undergoing ring-opening polymerization. 2,2-Bis(methylol)propionic acid (bis-MPA) is first converted (i) to a benzyl ester Bn-MPA, followed by reaction (ii) of Bn-MPA with triphosgene to form a cyclic carbonyl monomer, MTC-OBn. MTC-OBn is debenzylated (iii) to produce the cyclic carbonyl carboxylic acid, MTC-OH. Two pathways are shown for forming an ester from MTC-OH. In the first pathway, (iv), MTC-OH is treated with a suitable carboxy activating agent, such as dicyclohexylcarbodiimide (DCC), which reacts with ROH to form MTC-OR in a single step. Alternatively, MTC-OH can be converted first (v) to the acid chloride MTCCl followed by treatment (vi) of MTCCl with ROH in the presence of a base to form MTC-OR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, CH$_2$Cl$_2$, $-78°$ C. to 0° C., 95% yield of MTC-OBn; (iii) Pd/C (10%), H2 (3 atm), EtOAc, room temperature, 24 hours, 99% yield of MTC-OH; (iv) ROH, DCC, THF, room temperature, 1 to 24 hours; (v) (COCl)$_2$, THF, room temperature, 1 hour, 99% yield of MTCCl; (vi) ROH, NEt$_3$, RT, 3 hours yields MTC-OR.

Using the above Scheme 1, MTCCl was reacted with 3-bromopropanol and ethanol to form the corresponding MTCOPrBr and MTCOEt. The haloesters were purified by

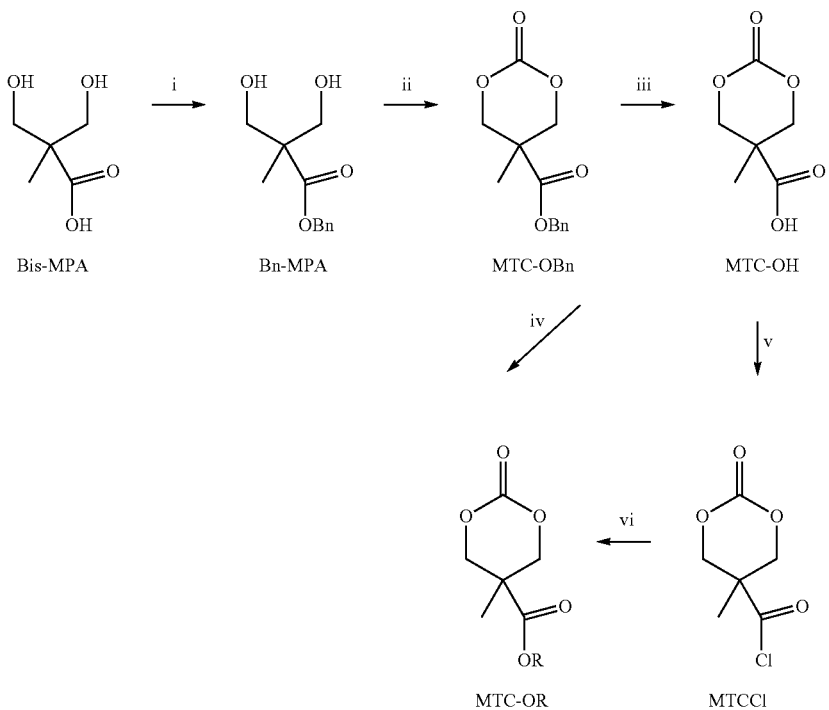

Scheme I.

either recrystallization or by flash chromatography (ethyl acetate/hexane) in high yields (>85%). MTC-OEt was used as a non-functional counterpart for dilution effects and to introduce hydrophobic blocks to the polymer for self-assembly.

MTCOEt (MW 188.2) has the structure.

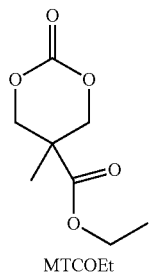

MTCOEt

MTCOEt
$^1$H NMR: delta 4.68 (d, 2H, CH$_2$OCOO), 4.25 (q, 1H, OCH$_2$CH$_3$), 4.19 (d, 2H, CH$_2$OCOO), 1.32 (s, 3H, CH$_3$), 1.29 (t, 3H, CH$_3$CH$_2$O). $^{13}$C NMR: delta 171.0, 147.5, 72.9, 62.1, 39.9, 17.3, 13.8. HR-ESI-MS: m/z calcd for C$_8$H$_{12}$O$_5$; Na, 211.0582. found, 221.0578.

MTC-OPrBr (MW 281.10) has the structure:

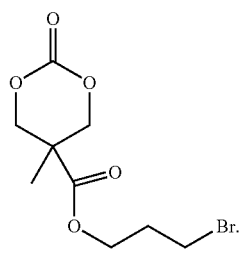

$^1$H NMR (400 MHz, CDCl$_3$): delta 4.69 (d, 2H; CH$_2$OCOO), 4.37 (t, 2H; OCH$_2$), 4.21 (d, 2H; CH$_2$OCOO), 3.45 (t, 2H; CH$_2$Br), 2.23 (m, 2H; CH$_2$), 1.33 (s, 3H; CH$_3$). $^{13}$C NMR (100 MHz, CDCl$_3$): delta 171.0, 147.3, 72.9, 63.9, 40.2, 31.0, 28.9, 17.3.

Polymer Characterization

Gel Permeation Chromatography (GPC)

GPC analysis of block copolymers was carried out with a Waters HPLC system equipped with a 2690D separation module, two Styragel HR1 and HR4E (THF) 5 micrometer columns (size: 300×7.8 mm) in series and a Waters 410 differential refractometer detector. The mobile phase used was THF with a flow rate of 1 mL/min. Number average molecular weights as well as polydispersity indices were calculated from a calibration curve using a series of polystyrene standards with molecular weight ranging from 1350 to 151700.

$^1$H NMR Analysis $^1$H NMR spectra of monomers and polymers were recorded on a Bruker Advance 400 NMR spectrometer at 400 MHz at room temperature. The $^1$H NMR measurements were carried out with an acquisition time of 3.2 seconds, a pulse repetition time of 2.0 seconds, a 30° pulse width, 5208-Hz spectral width, and 32 K data points. Chemical shifts were referred to the solvent peaks (delta=7.26 and 2.50 ppm for CDCl$_3$ and DMSO-d$_6$, respectively).

Synthesis of Monomers

The detailed synthetic procedures of monomers (MTC-OPrBr and MTC-OEt) used in this study can be found R. C. Pratt, et al., Chemical Communications, 2008, 114-116.

Polymer Synthesis and Characterization

In order to study the effect of hydrophilicity (cationic charge)/hydrophobicity balance in polycarbonate polymers on antibacterial and antifouling activities, three polymers with various hydrophobic contents and the same number of cationic repeat units were synthesized. Cationic polymer precursors with various compositions were synthesized by organocatalytic ring-opening polymerization (ROP) of two functional cyclic carbonates MTC-OEt and MTC-OPrBr, as shown in Scheme 2.

Scheme 2.

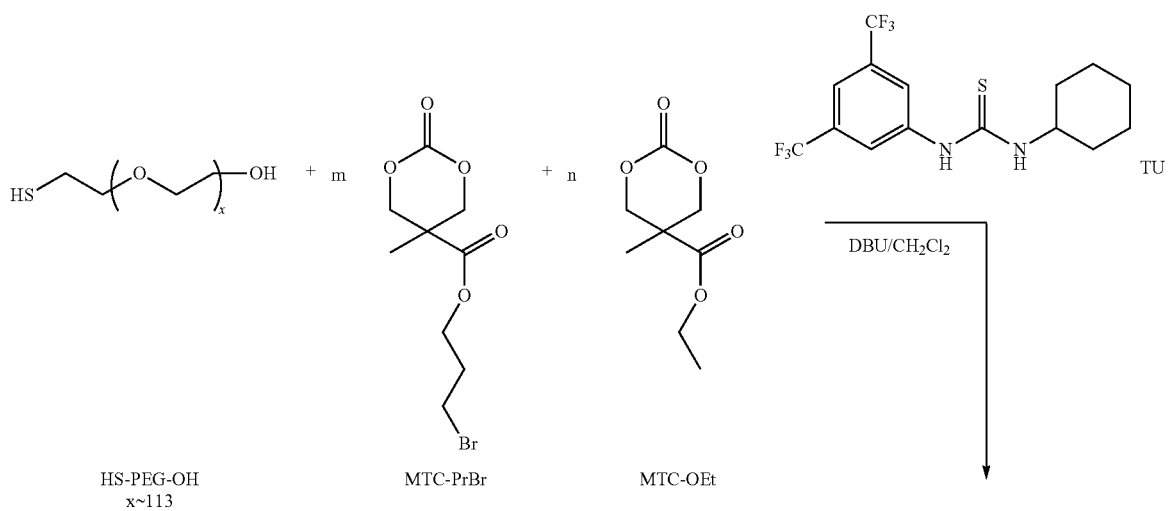

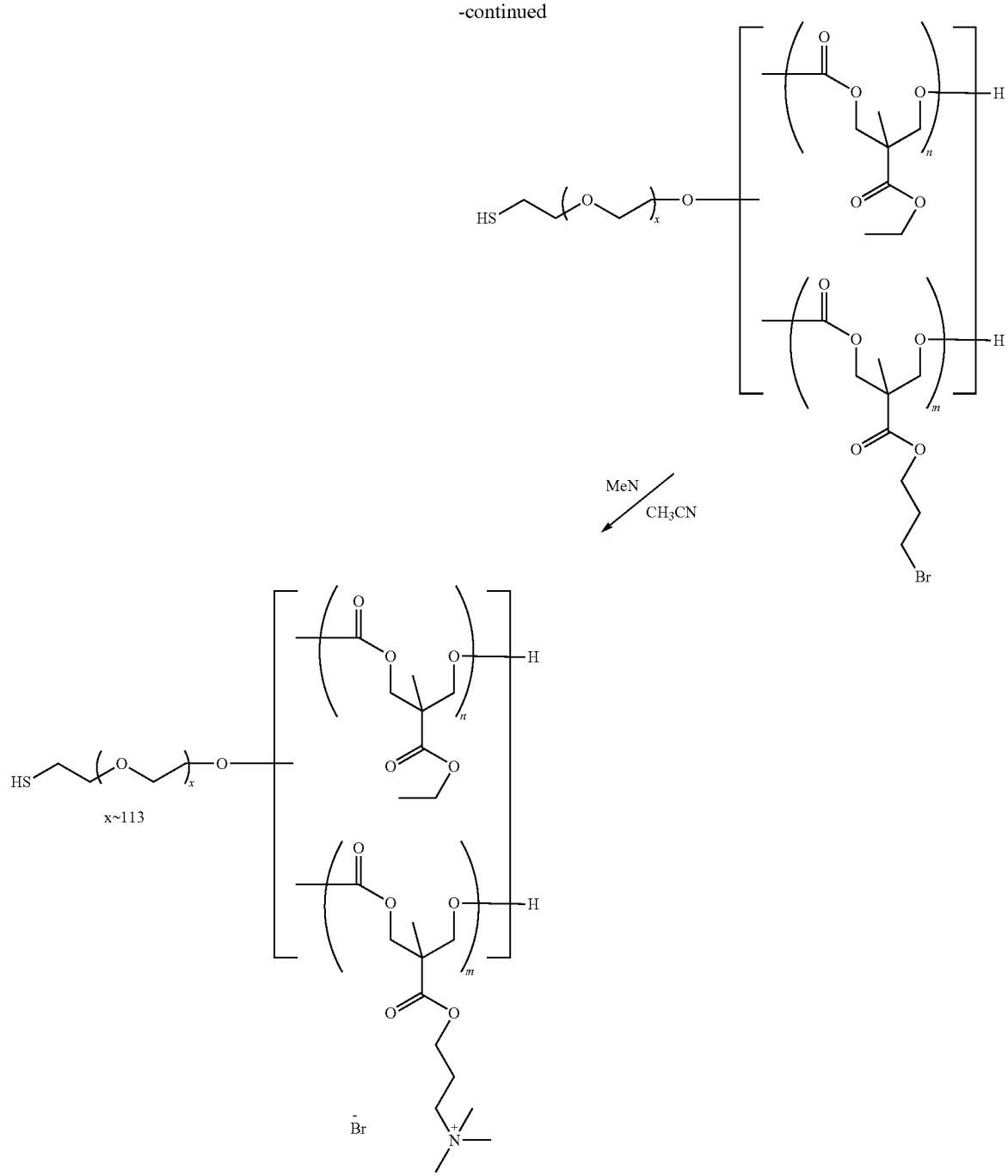

P-1: m = 18, n = 26
P-2: m = 18, n = 10
P-3: m = 18, n = 0

Cationic polymers with various compositions were synthesized through metal-free organocatalytic ring opening polymerization of MTC-OPrBr and MTC-OEt monomers using HS-PEG-OH as the macroinitiator in the presence of TU and DBU catalysts (Scheme 2). The resulting polymers were quaternized with trimethylamine to obtain the cationic polycarbonate diblock copolymers.

The details of the procedure for the preparation of P-2 are representative. In a glove-box, 0.3 g (0.06 mmol) of HS-PEG-OH initiator, 0.338 g (1.2 mmol) of MTC-PrBr (for a target degree of polymerization (DP) of 20), and 0.113 g (0.6 mmol) of MTC-OEt (for a target degree of polymerization (DP) of 10) were charged in a 20 mL glass vial equipped with a stir bar. Dichloromethane was added and the concentration was adjusted to 2 M with respect to the monomer. Once the initiator and monomers were completely dissolved, 22.2 mg (0.06 mmol) of TU and 9 mL (0.06 mmol) of DBU was added to catalyze the polymerization. After 5 hours, 5-10 mg of benzoic acid was added to quench the polymerization, after which the crude product was taken out off the glove-box, and purified by column chromatography on a SEPHADEX LH-20 column with THF as eluent, to give a colorless and sticky liquid (0.7 g, 93%) as P-2 precursor (HS-PEG-b-[P(MTC-OPrBr)$_{18}$-r-P(MTC-OEt)$_{10}$]. PDI: 1.19. $^1$H NMR (400 MHz, CDCl$_3$, 22° C.): delta 4.31 (m, 168H, H of —CH$_2$OCOO— and —OCH$_2$—), 3.65 (s, 455H, H of -PEG-), 3.47 (t, 36H, —CH$_2$Br), 2.19 (m, 36H, —CH$_2$CH$_2$Br), 1.27 (m, 60H, —CH$_3$).

The resulting P-2 precursor (0.7 g, about 0.06 mmol) was dissolved in acetonitrile (50 mL) and the solution was transferred (under nitrogen) into a 100 mL pressure safe Schlenk tube equipped with a stir bar. Under nitrogen the solution was cooled with dry ice, after which trimethylamine (about 0.5 g) was condensed into the Schlenk tube that was then sealed. The solution was held overnight under stirring. Following the reaction the solution was cooled to ambient temperature and nitrogen was bubbled through to remove excess trimethylamine. The solvent was removed by rotational evaporation, and the obtained product (P-2) was dried in a vacuum oven until a constant weight was reached (0.76 g, about 100%). $^1$H NMR (400 MHz, DMSO-d$_6$, 22° C.): delta 4.07-4.25 (m, br, 168H, H of —CH$_2$OCOO— and —OCH$_2$—), 3.39 (s, 491H, H of —CH$_2$N$^+$— and -PEG-), 3.06 (s, 162H, —N$^+$CH$_3$), 2.03 (s, 36H, —CH$_2$CH$_2$N$^+$—), 1.14 (m, 60H, —CH$_3$).

P-1 precursor (HS-PEG-b-[P(MT-OPrBr)$_{18}$-r-P(MTC-OEt)$_{26}$]), PDI: 1.23; Yield, 0.83 g, 90%. $^1$H NMR (400 MHz, CDCl$_3$, 22° C.): delta 4.30 (m, 264H, H of —CH$_2$OCOO— and —OCH$_2$—), 3.63 (s, 455H, H of -PEG-), 3.44 (t, 36H, —CH$_2$Br), 2.18 (m, 36H, —CH$_2$CH$_2$Br), 1.27 (m, 210H, —CH$_3$).

P-1, Yield, 0.88 g, about 100%. $^1$H NMR (400 MHz, DMSO-d$_6$, 22° C.): delta 4.08-4.26 (m, br, 264H, H of —CH$_2$OCOO— and —OCH$_2$—), 3.50 (s, 491H, H of —CH$_2$N$^+$— and -PEG-), 3.06 (s, 162H, —N$^+$CH$_3$), 2.04 (s, 36H, —CH$_2$CH$_2$N$^+$—), 1.16 (m, 210H, —CH$_3$).

P-3 precursor (HS-PEG-b-P(MTC-OPrBr)$_{18}$), PDI: 1.26; Yield, 0.60 g, 94%. $^1$H NMR (400 MHz, CDCl$_3$, 22° C.): delta 4.29 (m, 108H, H of —CH$_2$OCOO— and —OCH$_2$—), 3.64 (s, 455H, H of -PEG-), 3.45 (t, 36H, —CH$_2$Br), 2.19 (m, 36H, —CH$_2$CH$_2$Br), 1.27 (m, 54H, —CH$_3$).

P-3, Yield, 0.88 g, about 100%. $^1$H NMR (400 MHz, DMSO-d$_6$, 22° C.): delta 4.12-4.31 (m, br, 108H, H of —CH$_2$OCOO— and —OCH$_2$—), 3.51 (s, 491H, H of —CH$_2$N$^+$— and -PEG-), 3.10 (s, 162H, —N$^+$CH$_3$), 2.06 (s, 36H, —CH$_2$CH$_2$N$^+$—), 1.20 (m, 54H, —CH$_3$).

Figure 3A:
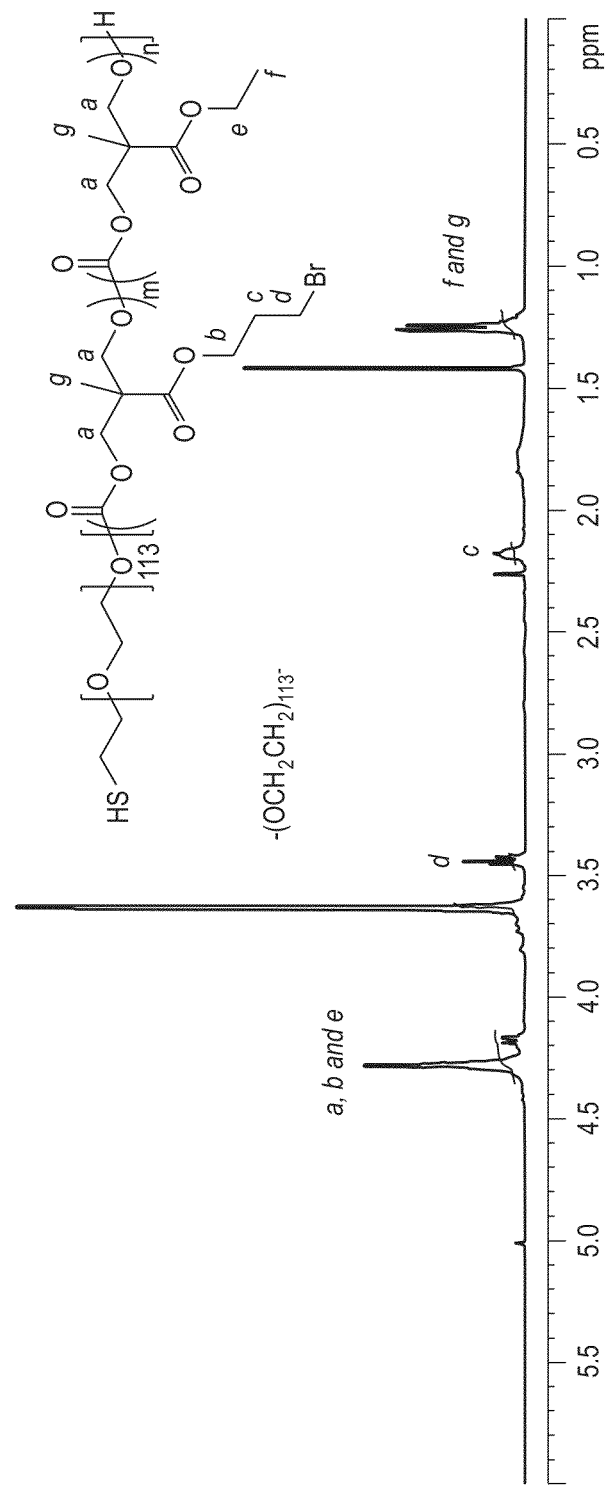
FIG. 3A is a $^1$H NMR spectrum of P-2 precursor (labeled A).
Figure 3B:
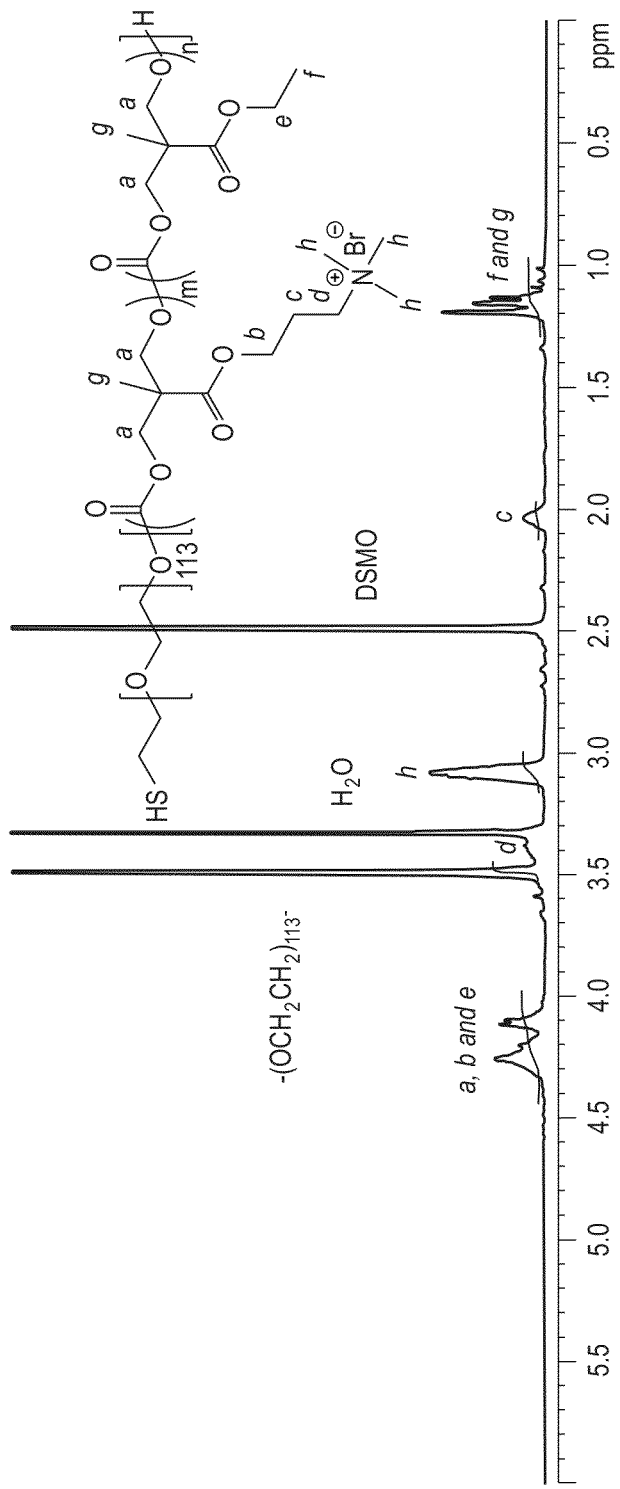
FIG. 3B is a $^1$H NMR spectrum of cationic polymer P-2 (labeled B).

The living and highly controlled nature of organocatalytic ROP method produced polymer compositions that matched well with initial monomer/initiator feed ratios. FIG. 3A is a $^1$H NMR spectrum of P-2 precursor (i.e., the non-quaternized polymer) that shows all peaks attributed to the HS-PEG fragment and carbonate repeat units having OEt and OPrBr pendent groups were clearly visible. Moreover, there was very good correlation between polymer integration values relative to original monomer concentrations. Since MTC-OEt and MTC-OPrBr had similar reactivity, it was assumed that both monomers were dispersed randomly in the polycarbonate block. All the polymer precursors had a narrow molecular weight distribution with polydispersity index (PDI) values ranging from 1.19 to 1.26. After isolation and purification, the polymer precursors were dissolved in anhydrous acetonitrile, and reacted with excess trimethylamine (TMA) in a pressure vessel. Finally, cationic polymers P-1, P-2, and P-3 having a thiol functional group on the distal end of the PEG fragment were isolated and dried in vacuo, removing all solvent and excess TMA. In the $^1$H NMR spectrum of P-2 (FIG. 3B), a new peak at 3.06 ppm was clearly observed that was attributed to the proton peak of methyl groups linked to the quaternary nitrogen. By comparing the integration of this peak with the peak at 2.03 ppm (H of —CH$_2$CH$_2$N$^+$ moiety), it was found that almost all the PrBr pendent groups in the polymer were aminated by TMA.

Preparation of Silicone Rubber

Silicone rubber samples were prepared by mixing and curing of the two-component kit SYLGARD-184 at high temperature. Base and curing agents in the kit were mixed thoroughly in 10:1 (w/w), followed by vacuum degas for half an hour. The mixture was cast in a Petri dish (for live/dead and scanning electron micrograph (SEM) studies), a 48-well plate (for colony assay) or a 96-well plate (for XTT assay), and kept overnight at 70° C. for curing. After curing, the rubber formed in Petri dish was cut into pieces of 0.5 cm×0.5 cm at a thickness of about 1 mm. Before usage, the silicone rubber surfaces were washed with ethanol and de-ionized (DI) water, followed by drying with nitrogen flow.

Polymer Coating on Silicone Rubber Surface

The cleaned silicone rubber surfaces were immersed in 2 mg/mL dopamine solution in 10 mM Tris-buffer (pH 8.5) for 24 hours. Before further treatment, the dopamine coated surfaces were rinsed with Tris-buffer three times. Cationic polymer (i.e., P-1, P-2 and P-3) and HS-PEG-OH at different concentrations were dissolved in 10 mM Tris-buffer (pH 8.5). The dopamine coated silicone rubbers were immersed in the colorless polymer solutions for 24 hours at 50° C. and then rinsed with Tris-buffer before further characterization. No color change or precipitate was observed in the polymer solution after 24 hours.

X-Ray Photoelectron Spectroscopy (XPS) Measurements

X-ray photoelectron spectroscopy (XPS, Kratos Axis HSi, Kratos Analytical, Shimadzu, Japan) with Al Ka source (hv=1486.71 eV) was used to analyze the surface chemistry of uncoated and coated rubber surfaces. The angle between the sample surface and detector was kept at 90°. The survey spectrum ranging from 1100 eV to 0 eV was acquired with pass energy of 80 eV. All binding energies were referenced to the C 1s (C—C bond) at 284.5 eV.

Static Contact Angle Measurements

The static contact angles on uncoated or polymer coated surfaces were measured by an OCA30 contact angle measuring device (Future Digital Scientific Corp., U.S.A.). DI water (20 microliters) was used for the measurements. All samples were analyzed in triplicate. The static contact angle data are presented as mean±SD.

Quartz Crystal Microbalance with Dissipation (QCM-D) Measurements

Thickness of the hydrated polymer layer on dopamine coated surfaces was determined by a QCM-D device (Q-sense E4, Sweden). Gold coated AT-cut quartz crystals with oscillating frequency of 4.95 MHz were used as sensors for the experiments. To clean the sensor surface, sensors were treated in an UV/Ozone chamber for 10 minutes, immersed in piranha solution (DI water, ammonia and hydrogen peroxide in a volume ratio of 5:1:1) at 75° C. for 5 minutes, rinsed with DI water, and dried with nitrogen gas. The clean sensors were immersed in dopamine solution (2 mg/mL in 10 mM Tris-buffer, pH 8.5) for 24 hours. The dopamine coated sensors were washed with Tris buffer three times and placed in the QCM-D chamber. Change in frequency (Δf) and dissipation (ΔD) was monitored during the flow of Tris-buffer. After stable f and D baselines were obtained, P-2 in 10 mM Tris-buffer (three different concentrations were tested) was flown over the dopamine coated sensors at a flow rate of 10 mL/min at 50° C. for 80 min. After polymer exposure, 10 mM Tris-buffer was pumped into the chamber to remove all loosely adhered polymer. The recorded f and D at four overtones (3, 5, 7 and 9) were analyzed using the software Q-tools. The polymer layer thickness was estimated using the Voigt viscoelastic model. For measurement of bovine serum albumin (BSA) adsorption on dopamine+P-2 coated surface, BSA in phosphate buffered saline (PBS, 50 mg/mL) was pumped into the chamber at a flow rate of 10 mL/min. When the frequency stabilized, PBS was pumped into the chamber to wash off loosely absorbed BSA. The frequency of the third overtone (f3) and dissipation (D3) was recorded and used to analyze BSA adsorption.

Colony Assay

The concentration of S. aureus in tryptic soy broth (TSB) was adjusted to give an initial optical density (OD) reading of 0.07 at the wavelength of 600 nm on a microplate reader (TECAN, Switzerland), which corresponds to the concentration of McFarland 1 solution ($3 \times 10^8$ CFU/mL). The bacterial solution was diluted by 100 times to achieve an initial loading of $3 \times 10^6$ CFU/mL. 20 microliters of the bacterial solution was added to each well of a 48-well plate, in which an uncoated or polymer coated silicone rubber was placed. The 48-well plate was incubated at 37° C. for 8 or 24 hours, after which 10 microliters of the bacterial solution was taken out from each well and diluted with an appropriate dilution factor. The diluted bacterial solution was streaked onto an agar plate (LB Agar from 1st Base). The number of the colony-forming units (CFUs) was counted after incubation for about 16 hours at 37° C. Each test was carried out in triplicate. Similarly, MRSA was cultured overnight in cation-adjusted Mueller-Hinton broth, and the MRSA solution with a concentration of ($6 \times 10^6$ CFU/mL) was used for colony assay.

Antifouling Activity Analysis of the Non-Coated and Coated Silicone Rubber Surfaces by XTT Reduction Assay A semi-quantitative measurement of live S. aureus on the surface was performed by analyzing 2,3-bis(2-methoxy-4-nitro-5-sulfo-phenyl)-2H-tetrazolium-5-carboxanilide (XTT) reduction. XTT assay is a method to measure the mitochondrial enzyme activity in live cells. During the assay, the optical density (OD) of orange colored formazan dye produced from XTT conversion by mitochondrial enzymes in viable cells was recorded. S. aureus (20 microliters, $3 \times 10^6$ CFU/mL) or MRSA (20 mL, $6 \times 10^6$ CFU/mL) were seeded onto uncoated and coated silicone rubber surfaces and cultured for 8 or 24 hours. The rubber samples were washed twice with sterile PBS and then incubated with 100 microliters of PBS, 10 microliters of XTT (1 mg/mL) and 2 microliters of menadione (0.4 mM) in each well at 37° C. for 2 hours. The mitochondrial dehydrogenase of the bacterial cells reduced XTT tetrazolium salt to formazan, and the colorimetric change correlated with the cell metabolic activity. The absorbance at a test wavelength of 490 nm and a reference wavelength of 660 nm of the samples was measured using a microplate reader (TECAN, Sweden.

LIVE/DEAD Baclight Bacterial Viability Assay of the Catheter Surfaces

A LIVE/DEAD Baclight bacterial viability kit (L-7012, Invitrogen) was used to assess the bacterial cell viability on the surfaces. In this assay, the red-fluorescent nucleic acid staining agent propidium iodide, which only penetrates damaged cell membrane, was used to label dead bacterial cells on the silicone rubber surface. In contrast, the SYTO 9 green-fluorescent nucleic acid staining agent, which can penetrate cells both with intact and damaged membranes, was used to label all the bacterial cells. The bacteria ($10^6$ cells/mL, 100 microliters) were seeded onto the uncoated and polymer coated silicone rubber surfaces, followed by incubation at 37° C. for 4 hours or 24 hours. The supernatant was removed, and the silicone rubber was washed with PBS buffer three times. They were then incubated in a 48-well plate with 200 microliters of a dyes-containing solution, which was prepared by adding 3 microliters of SYTO (3.34 mM) and 3 microliters of propidium iodide (20 mM) to 2 mL of PBS buffer at room temperature in the dark for 15 minutes. The stained bacterial cells were examined under a Zeiss LSM 5 DUO laser scanning confocal microscope (Germany). Images were obtained using an oil immersed 40x object lens under the same conditions.

Evaluation of Biofilm Formation by Scanning Electron Microscopic (SEM) Observations To study the biofilm formation and attachment of S. aureus on uncoated and polymer coated silicone rubber surfaces, the surfaces were incubated with S. aureus for 7 days and then examined using SEM. Dopamine, dopamine+HS-PEG-OH, and dopamine+cationic polymer P-1, P-2 and P-3 coated silicone rubber and uncoated silicone rubber surfaces were prepared by following the same procedures described above. Bacteria ($10^6$ cells/mL, 100 microliters) were seeded onto uncoated and polymer coated silicone rubbers and incubated at 37° C. for 7 days. The culture medium TSB was changed every 24 hours. After the incubation, the samples were washed with sterile PBS three times, followed by fixation with 2.5% glutaraldehyde in PBS for 2 hours. The fixed bacteria were dehydrated with a series of graded ethanol solution (25%, 50%, 75%, 95%, and 100%, 10 minutes each) before platinum coating. A field emission scanning electron microscope (FE-SEM, JEOL JSM-7400F, Japan) was used for SEM analysis.

Analysis of Platelet Adhesion

Fresh rat blood was centrifuged at 1000 rpm/min for 10 minutes to obtain platelet-rich plasma (PRP). Uncoated silicone rubber and dopamine+P-2 coated silicone rubber surfaces were immersed in PRP and incubated at 37° C. for 0.5 hours. After the incubation, the samples were washed with PBS three times, followed by the same fixation procedure and SEM observation described above.

Static Hemolysis Assay

Fresh rat blood was obtained and diluted to 4% (by volume) with PBS buffer. The red blood cell suspension in PBS (100 microliters) was placed on the pristine and polymer coated silicone rubber surfaces in each well of a 96-well plate, and 100 microliters of PBS was then added to each well. The plate was incubated for 1 hour at 37° C. to allow hemolysis to take place. After incubation, the 96-well plate was centrifuged at 2200 rpm for 5 minutes. Aliquots (100 mL) of the supernatant from each well of the plate were transferred to a new 96-well plate, and hemoglobin release was measured at 576 nm using the microplate reader (TECAN, Sweden). In this assay, the red blood cells in PBS were used as a negative control and red blood cells lysed with 0.2% TRITON-X were used as a positive control. Absorbance of wells with red cells lysed with 0.2% TRITON X was taken as 100% hemolysis. Percentage of hemolysis was calculated using the following formula: Hemolysis (%)=[($OD_{576\ nm}$ of the sample–$OD_{576\ nm}$ of the negative control)/($OD_{576\ nm}$ of the positive control–$OD_{576\ nm}$ of the negative control)]×100. The data were expressed as mean and standard deviation of three replicates.

Results

Surface Wettability

Figure 4:
FIG. 4 is a table of static water contact angles and the images of the drops measured for the uncoated silicone rubber, dopamine coated silicon rubber (labeled "PDA coating" for polydopamine), and dopamine+cationic polymer P-1 to P-3 (labeled "P-1 coating," "P-2 coating," and "P-3 coating," respectively).
Figure 4:
Figure 4:
Figure 4:
Figure 4:

To examine the surface wettability change of the silicone rubber after applying the polymer coating, the static water contact angle of the silicone rubber was measured. As listed in the table of FIG. 4, the static contact angle of uncoated silicone rubber surface was 106.3±3.2°, indicating a hydrophobic surface. After applying the dopamine (labeled "PDA Coating" for polydopamine formed by the treatment), the silicone rubber surface became relatively more hydrophilic with a significantly reduced contact angle) (53.3±0.2°. This wettability change is in agreement with earlier observations (Lee, et al., Science 2007, 318, pages 426-430). Thiol-terminated PEG-b-cationic polycarbonates (i.e., P-1, P-2 and P-3) were attached onto the dopamine coated surface to obtain an antimicrobial and antifouling coating layer. The static contact angles of the surfaces coated with P-1, P-2 and P-3 increased slightly to 68.9±2.0°, 68.3±1.0° and 71±2.6° respectively, indicating that the surfaces were still hydrophilic after coating the cationic polymer on the dopamine treated silicone rubber. The increase in the surface hydrophobicity after coating the cationic polymer might be due to the introduction of hydrophobic polycarbonate backbone. In addition, it was observed that the content of the hydrophobic monomer MTC-OEt did not affect the contact angle significantly.

Surface Chemical Composition

Figure 5A:
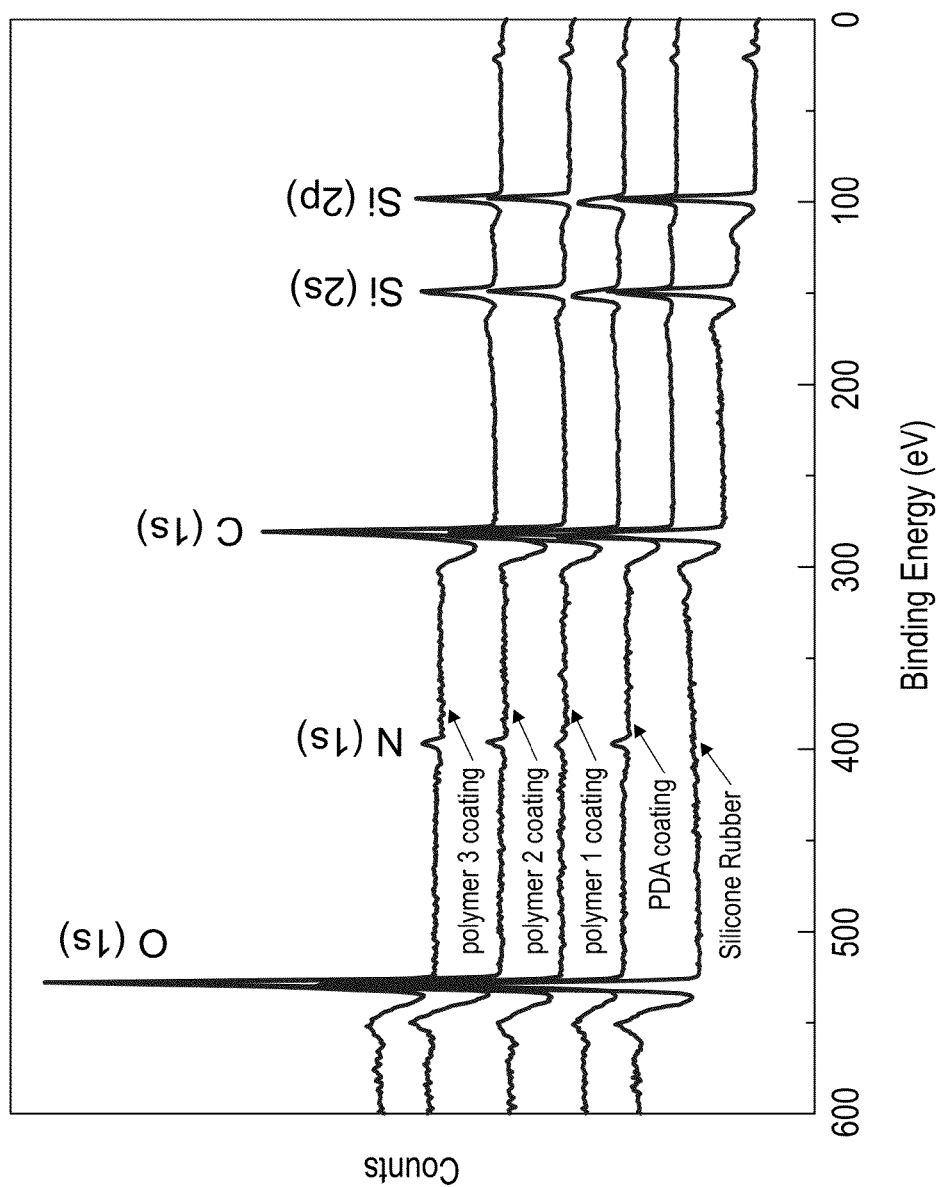
FIGS. 5A to 5C are x-ray photoelectron spectroscopy (XPS) spectra.

To further verify successful coating of polymers, the XPS spectra of silicone rubber before and after polymer coating were analyzed. As shown in FIG. 5A, C1s, O1s, Si2s and Si2p peaks were present. Upon coating dopamine, a new peak appeared at binding energy of 396.7 eV, which corresponds to N1s, thus proving that dopamine was successfully coated on the silicone rubber surface. After dopamine treatment, the carbon atomic content increased from 48.7% to 59.1% and the silicon atomic content decreased from 22.8% to 13.4% because dopamine has a higher carbon content compared to silicone rubber. Table 6 compares the analysis of the silicone rubber substrate, the treated substrate after coating with dopamine, and the antimicrobial silicone rubber after stepwise application of the cationic polymer to the dopamine treated substrate.

TABLE 6

|  | Silicone rubber | Dopamine coated Silicone | dopamine + P-1 coated silicone | dopamine + P-2 coated silicone | dopamine + P-3 coated silicone |
| --- | --- | --- | --- | --- | --- |
| C (1s) | 48.7 | 59.1 | 58.5 | 59.7 | 58.0 |
| N (1s) | 0.0 | 3.3 | 1.9 | 2.0 | 2.5 |
| O (1s) | 28.5 | 24.2 | 28.2 | 25.3 | 25.0 |
| Si (2p) | 22.8 | 13.4 | 11.3 | 12.9 | 14.5 |

Figure 5B:
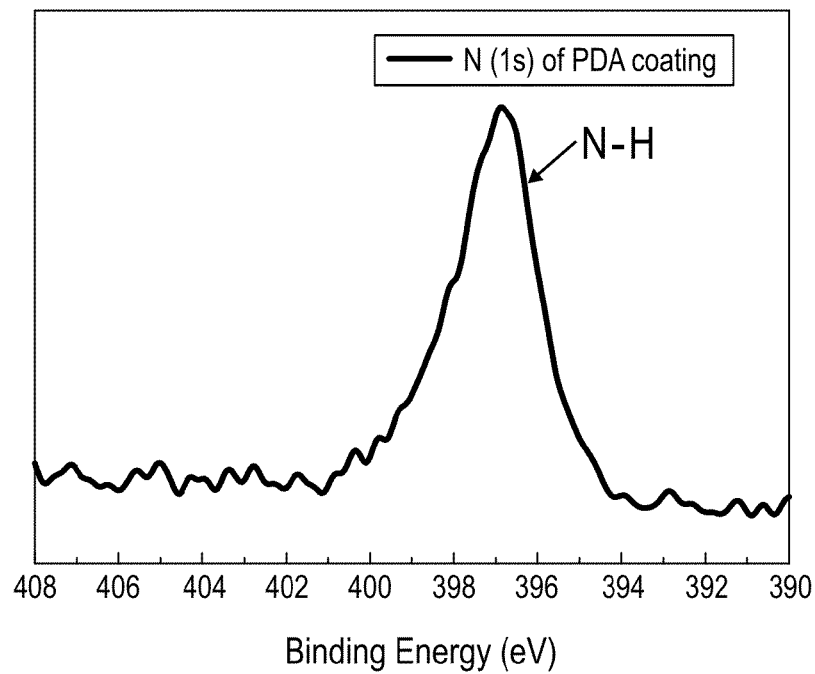
Figure 5C:
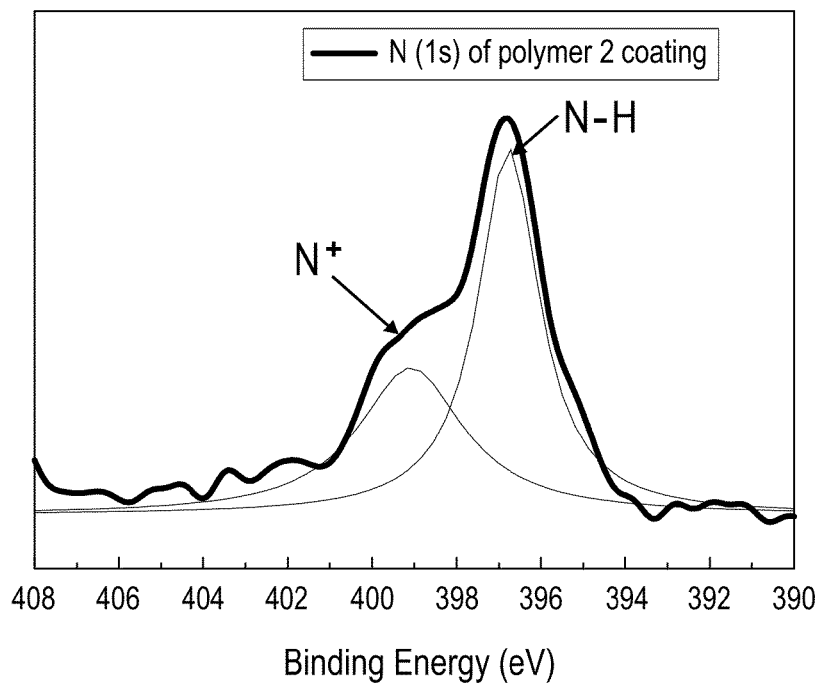

These findings indicate successful coating of dopamine. In addition, the three polymer coated surfaces showed similar spectra, which consist of C1s, O1s, Si2s, Si2p and N1s peaks (FIG. 5A). The nitrogen content of the dopamine+cationic polymer decreased slightly as compared to that of dopamine coating (Table 6). This difference was due to the lower nitrogen content of the polymers. In the high-resolution N1s spectra of the dopamine coated silicone (FIG. 5B) and dopamine+P-2 coated silicone (FIG. 5C), a peak at 396.7 eV was found that relates to the N—H bond. In the spectrum of the P-2 coating, another peak at 399.1 eV was observed, which corresponds to nitrogen ion (i.e., $N^+$) in the polymer, further proving the successful polymer coating.

Polymer Coating Thickness

Figure 6:
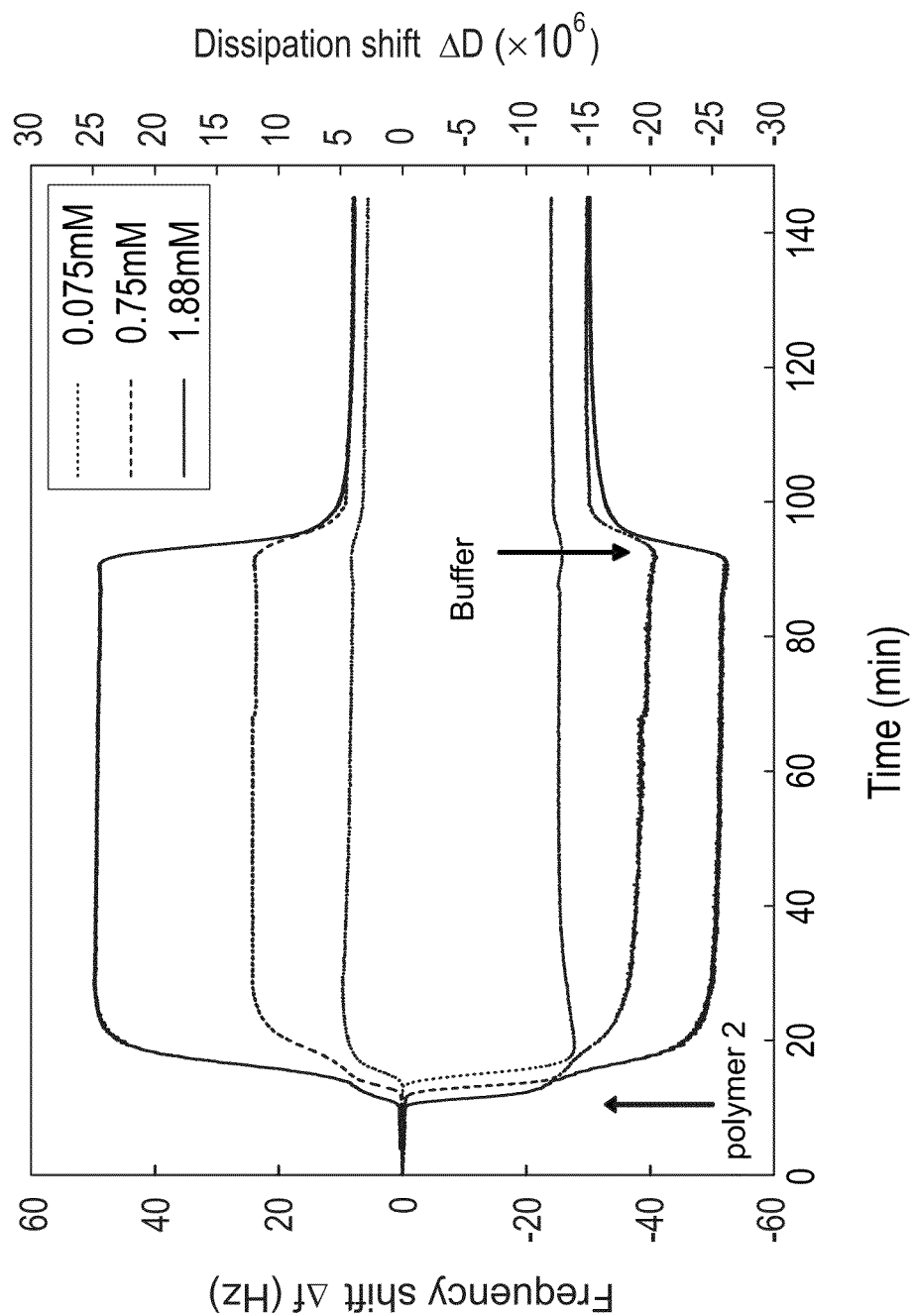
FIG. 6 is a graph quartz crystal microbalance analysis showing the frequency shift (Δf) and dissipation shift (ΔD) of the 3rd overtone as a function of time after coating at various concentrations of P-2 on the dopamine coated silicon rubber.
Figure 7:
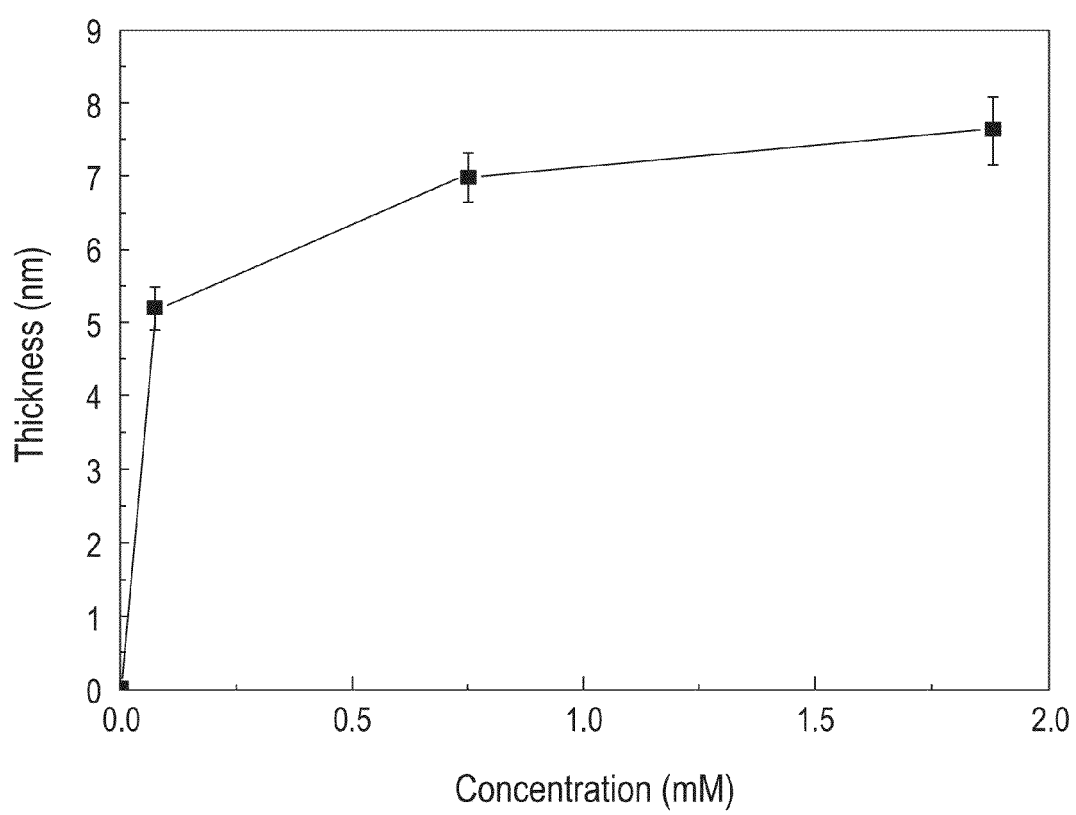
FIG. 7 is a graph showing the hydrated thickness of the P-2 coatings of FIG. 6 as a function of P-2 concentration.

The change in the hydrated polymer coating thickness was monitored by quartz crystal microbalance and dissipation monitoring (QCM-D) in real time as a function of polymer concentration. As shown in FIG. 6, the frequency (f) decreased and the dissipation (D) increased when polymer solutions at different concentrations were injected into the QCM-D chambers, suggesting that polymer was grafted onto the dopamine-treated silicone surface, resulting in the increase in mass and softness. In addition, larger f and D shifts were seen as the polymer concentration increased. This difference was due to the larger quantity of polymer immobilized on the surfaces at higher concentrations. After about 20 min, stable f and D were obtained, showing the saturation of the surfaces. To wash off loosely bound cationic polymer from the surfaces, Tris buffered saline (TBS) was injected into the chambers. As expected, f increased and D decreased, suggesting mass and softness decreased. When the final equilibrium was obtained, the difference in f and D shift between different polymer concentrations was observed. The total change of f value at polymer concentrations of 0.075, 0.75 and 1.88 mM was about 24, 30 and 30 Hz respectively, and the total change of D value was 2.8, 4, and 4 respectively. These values suggest that grafting at higher polymer concentrations (0.75 and 1.88 mM) resulted in more polymer being immobilized on the surface. The polymer coating thickness at different concentrations at the equilibrium state was calculated using the viscoelastic model. As shown in FIG. 7, the hydrated polymer coating thickness increased from 5.2 to 7.0 nm when the polymer concentration was raised from 0.075 to 0.75 mM. After further increasing polymer concentration to 1.88 mM, a relatively small increase in thickness was observed.

Antibacterial Activity of Polymer Coatings Against S. aureus

Figure 8:
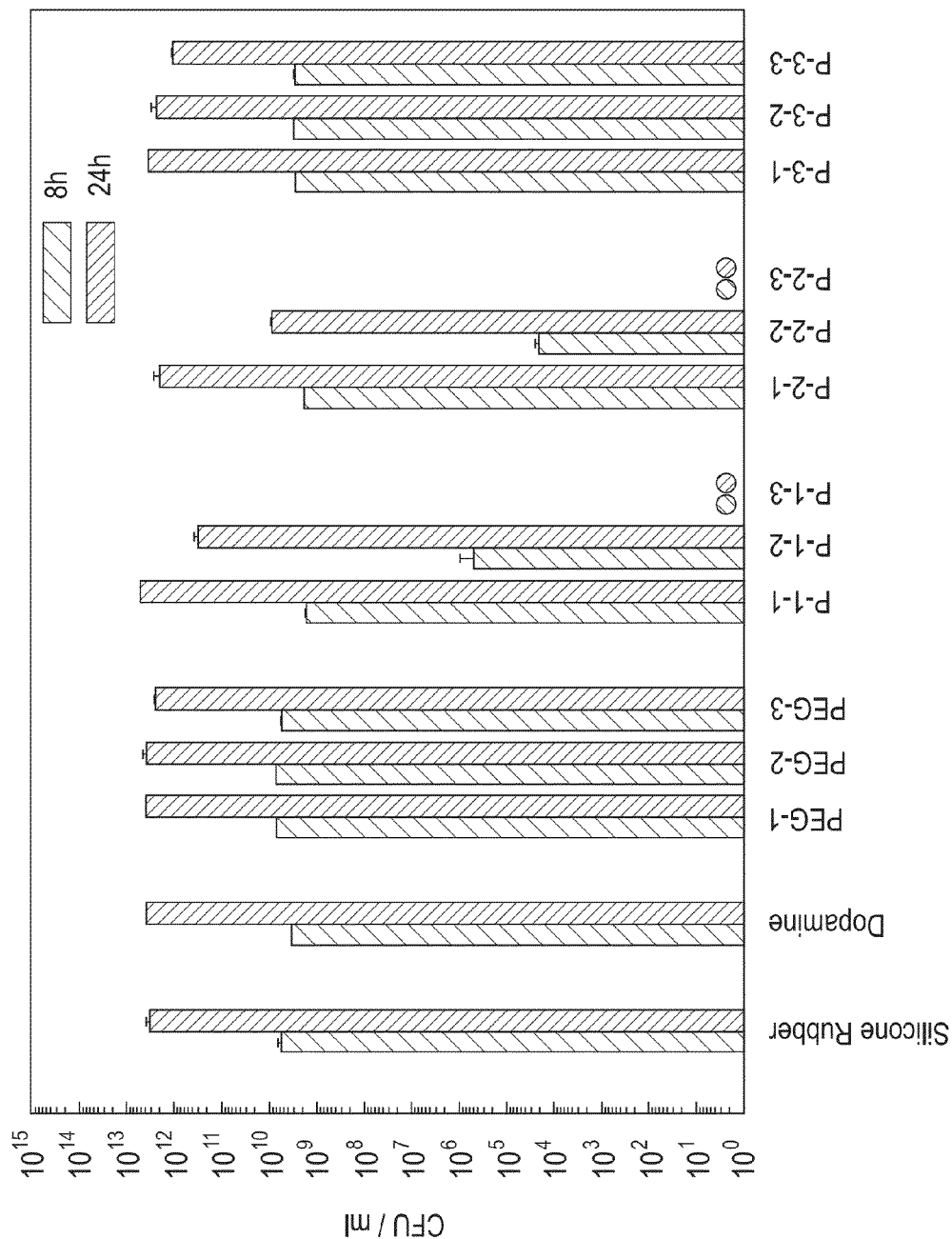
FIG. 8 is a bar chart showing the number of *Staphylococcus aureus* (*S. aureus*) colonies remaining in solution after 8 hours and 24 hours incubation with the uncoated silicone rubber, dopamine coated silicone rubber, silicone rubber coated with dopamine+HS-PEG-OH (labeled "PEG"), and silicone rubber coated with dopamine+cationic polymer P-1 to P-3. The labels -1, -2, or -3 following the polymer names correspond to polymer concentrations of 0.075, 0.75 and 1.88 mM used to make the coatings, respectively. Patterned circles indicate no colonies were found.

The colonies of S. aureus in the solution after 8 hours or 24 hours of incubation with untreated and treated silicone rubber were counted to determine the antibacterial activity of polymer coatings. The bar chart of FIG. 8 shows the number of colonies in the solution incubated with the untreated silicone rubber at 8 hours and 24 hours was $5.4 \times 10^9$ CFU/mL and $3.3 \times 10^{12}$ CFU/mL respectively, approximating the results obtained with silicone rubber coated only with dopamine ($3.4 \times 10^9$ CFU/mL and $3.9 \times 10^{12}$ CFU/mL respectively). For the silicone rubber coated with dopamine+HS-PEG-OH at various polymer concentrations, the number of bacterial colonies in solution was about $6 \times 10^9$ CFU/mL and $3 \times 10^{12}$ CFU/mL respectively, suggesting that HS-PEG-OH coating also did not kill the bacteria in the solution. The silicone rubbers coated with dopamine+cationic polymer P-1 and dopamine+cationic polymer P-2 exhibited antibacterial activity in solution when the cationic polymer concentration used to prepare the coating was 0.75 and 1.88 mM. In particular, when the surface was coated with dopamine+cationic polymer P-1 or dopamine+cationic polymer P-2 at cationic polymer concentration 1.88 mM, no colony was found at both 8 hours and 24 hours. However, the coating with cationic polymer P-3 that contained no hydrophobic monomer showed no antibacterial activity in solution even at the highest concentration.

Antifouling Activity of Polymer Coatings Against S. aureus

Figure 9:
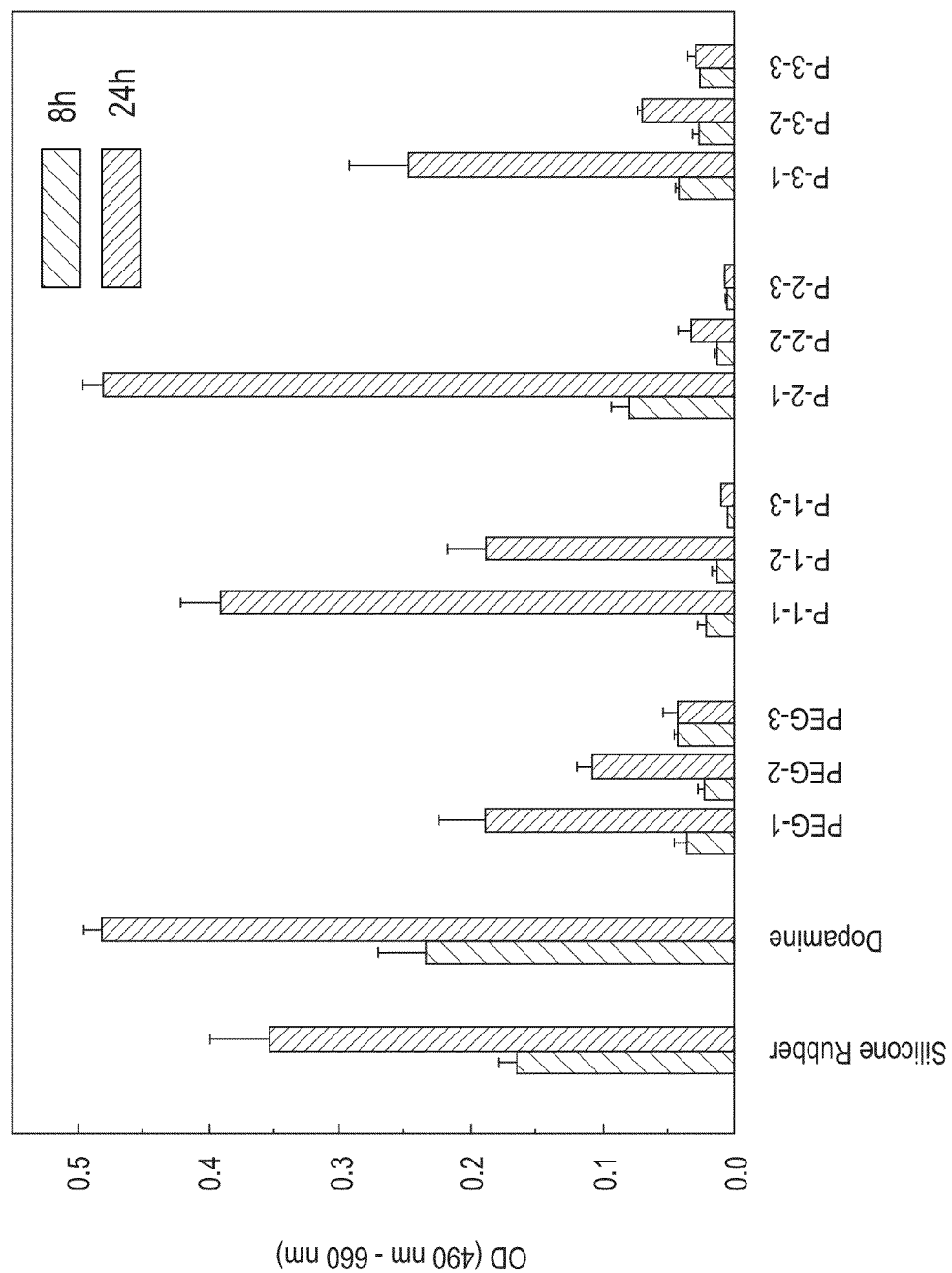
FIG. 9 is a bar chart showing the number of *Staphylococcus aureus* (*S. aureus*) colonies after 8 hours and 24 hours incubation with the uncoated silicone rubber, dopamine coated silicone rubber, silicone rubber coated with dopamine+HS-PEG-OH (labeled "PEG"), and silicone rubber coated with dopamine+cationic polymer P-1 to P-3. The labels -1, -2, or -3 following the polymer names correspond to polymer concentrations of 0.075, 0.75 and 1.88 mM used to make the coatings, respectively.

To examine the bacterial adhesion and growth on uncoated and polymer coated silicone rubber surfaces, an XTT assay was performed. The XTT assay is a widely used method to determine bacterial cell viability. In this assay, a higher optical density (OD) reading correlates to more live cells adhered to the surface. As shown in FIG. 9, the OD reading of uncoated silicone rubber was about 0.17 after 8 hours of incubation, which increased to 0.35 at 24 hours. This suggests that a relatively small number of viable bacterial cells attached on the surface after 8 hours, and the cell number significantly increased at 24 hours. These results indicate that silicone rubber surfaces are prone to S. aureus adhesion and growth. The higher OD value with dopamine coated rubber at 8 and 24 hours indicated higher affinity of S. aureus to the dopamine treated silicone rubber. The dopamine-enhanced cell attachment was previously observed for mammalian cells. For the silicone surfaces coated with dopamine+HS-PEG-OH or dopamine+P-3 (without a hydrophobic component) at 1.88 mM, medium antifouling activity was observed, with OD values of 0.03 and 0.04 respectively after 24 hours of incubation. However, coatings made with dopamine+P-1 and dopamine+P-2 demonstrated greater antifouling activity, having OD values less than 0.01, suggesting that the incorporation of hydrophobic monomer in the cationic polymer enhances antifouling activity. The antifouling activity of the polymer coatings most likely comes from PEG. This nonfouling property is due to the flexible chain and large steric repulsive forces of PEG molecules that prevent microbial cells from approaching the substrate. The improved antifouling efficiency seen with the cationic P-1 and cationic P-2 coatings is probably due to the antibacterial activity of polymers with hydrophobic components, which might synergistically prevent bacterial cell fouling.

Figure 10:
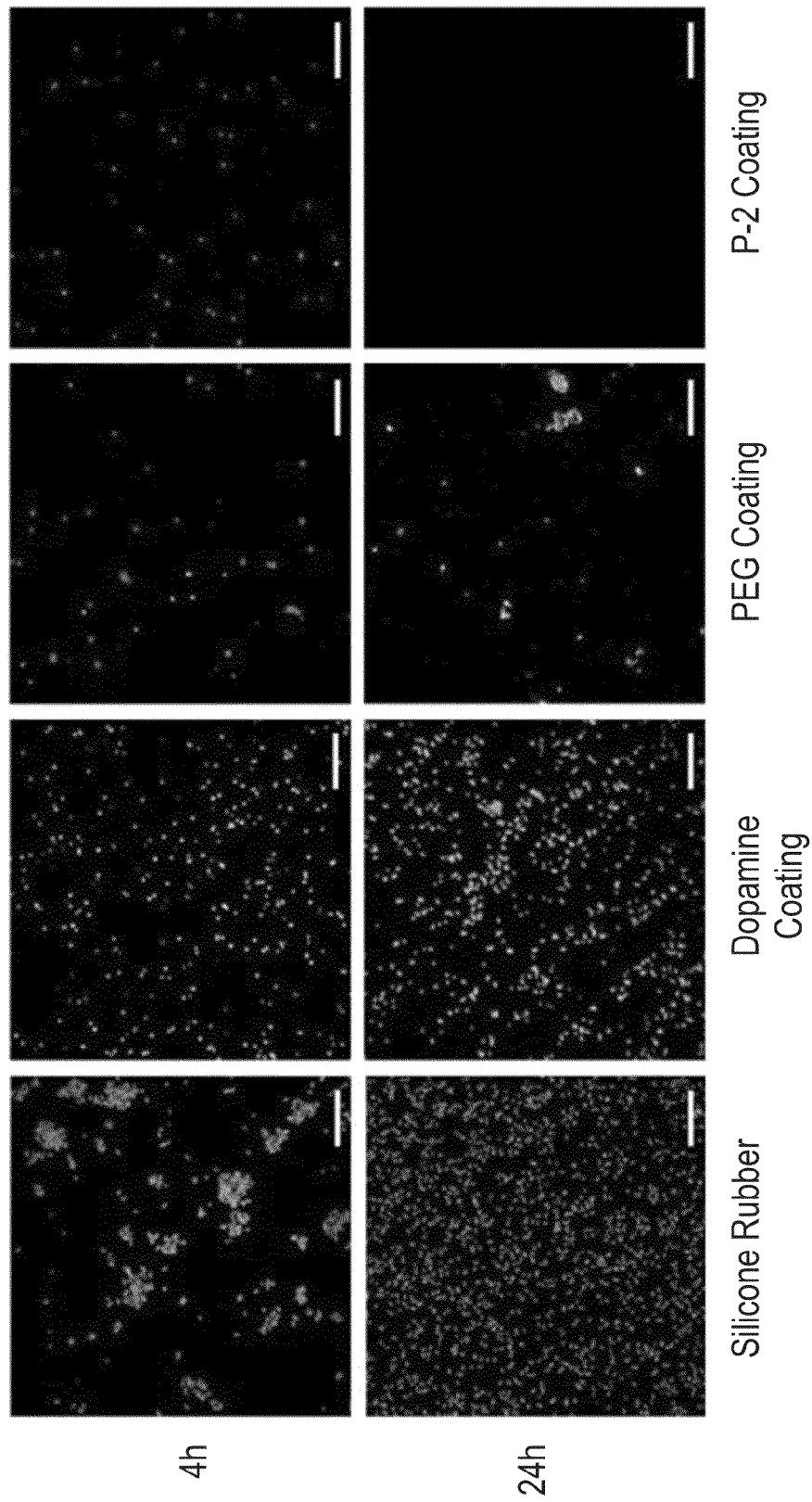
FIG. 10 is a set of images showing the LIVE/DEAD cell staining on the uncoated silicone rubber surface and silicone rubber surfaces coated with dopamine (labeled "Dopamine Coating"), dopamine+HS-PEG-OH (labeled "PEG Coating"), and dopamine+P-2 (labeled "P-2 Coating") after 4 hours and 24 hours of incubation with *S. aureus*. The size of the scale bars is 10 micrometers.

To further confirm the antifouling property of polymer coated silicone rubber surfaces, LIVE/DEAD backlight bacterial viability assay was performed. From FIG. 10, a large number of live bacterial cells (green dots) can be found on the uncoated and dopamine coated surfaces, especially after 24 hours of incubation. However, there were no live bacterial cells found on the dopamine+P-2 coated rubber surface after 24 hours of incubation, indicating excellent antifouling activity of the polymer coating. Although there were a significantly lower number of live bacterial cells found on the dopamine+HS-PEG-OH coated surface at 4 hours as compared to the uncoated and dopamine coated surfaces, there were still live bacterial cells found at 24 hours. These results suggest better antifouling activity of the dopamine+P-2 coating than the dopamine+HS-PEG-OH coating, which is in agreement with the XTT assay findings.

Antibacterial and Antifouling Activities Against MRSA

Figure 11:
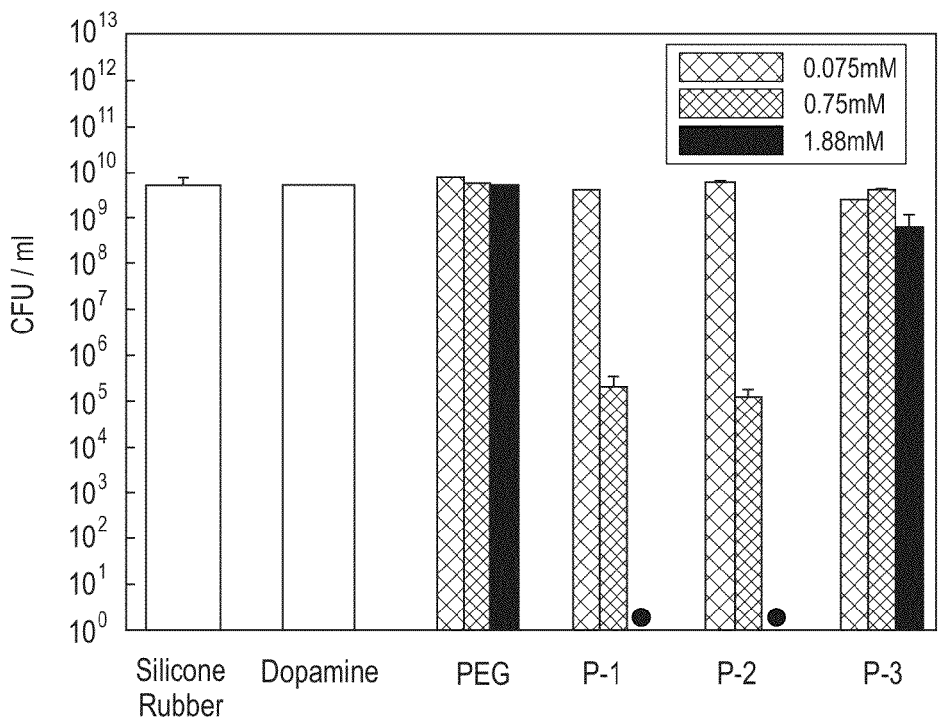
FIG. 11 is a bar graph showing the antibacterial and antifouling activities of polymer coatings at different polymer concentrations against MRSA in solution in terms of colony forming units (CFU) per milliliter after 8 hours of incubation. The bar chart compares uncoated silicone rubber surface and silicone rubber surfaces coated with dopamine (labeled "Dopamine"), dopamine+HS-PEG-OH (labeled "PEG"), and dopamine+cationic polymer P-1 to P-3. Patterned circles indicate no colonies found.
Figure 12:
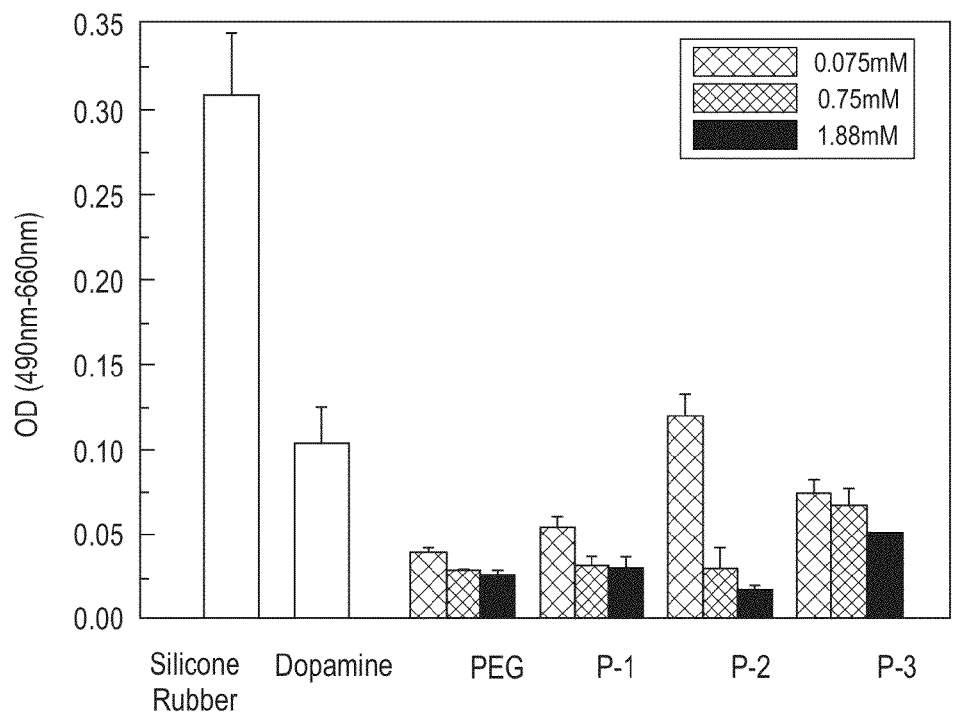
FIG. 12 is a bar graph showing the antibacterial and antifouling activities of polymer coatings at different polymer concentrations against MRSA in solution, in terms of optical density (OD) at 490 nm-660 nm after 8 hours of incubation. The bar chart compares uncoated silicone rubber surface and silicone rubber surfaces coated with dopamine (labeled "Dopamine"), dopamine+HS-PEG-OH (labeled "PEG"), and dopamine+cationic polymer P-1 to P-3.

Similar to the results of *S. aureus*, dopamine only and dopamine+HS-PEG-OH coatings prepared using various HS-PEG-OH concentrations did not show antibacterial activity against MRSA as compared to untreated silicone rubber, with over $5.0 \times 10^9$ CFU/mL detected (FIG. 11, bar chart). However, the surfaces coated with dopamine+P-1 and dopamine+P-2 at cationic polymer concentrations of 0.75 mM and 1.88 mM demonstrated antibacterial activity against MRSA. More importantly, the surfaces coated with dopamine+P-1 and dopamine+P-2 at the concentration of 1.88 mM killed all the MRSA in the solution. In contrast, the surface coated with dopamine+P-3 did not show apparent antibacterial activity at any P-3 concentration. As shown in the bar chart of FIG. 12, the OD value of uncoated silicone rubber was about 0.30 after 8 hours of incubation, indicating silicone rubber surface was more prone to MRSA adhesion and growth than *S. aureus*. Compared to the uncoated surface, the dopamine coated silicone surface exhibited a lower OD reading of 0.1, which suggests that less MRSA was attached. The silicone surfaces coated with dopamine+HS-PEG-OH at various HS-PEG-OH concentrations showed more apparent antifouling activity with OD value of around 0.03. The dopamine+P-1 coatings and dopamine+P-2 coatings prepared at cationic polymer concentration of 0.75 mM demonstrated similar antifouling activity to that observed for the dopamine+HS-PEG-OH coating, and the surface coated with dopamine+P-2 at a concentration of 1.88 mM demonstrated even greater antifouling activity than the dopamine+HS-PEG-OH coating, with (optical density) OD value of 0.018. Among all the polymers, the dopamine+P-3 coating showed the least antifouling activity even at the highest P-3 concentration. These findings prove that the surfaces coated with dopamine+P-1 and dopamine+P-2, which have hydrophobic monomer MTC-OEt, at high concentrations not only killed planktonic MRSA in solution, but also inhibited MRSA fouling on the surfaces.

Prevention of Biofilm Formation

Figure 13:
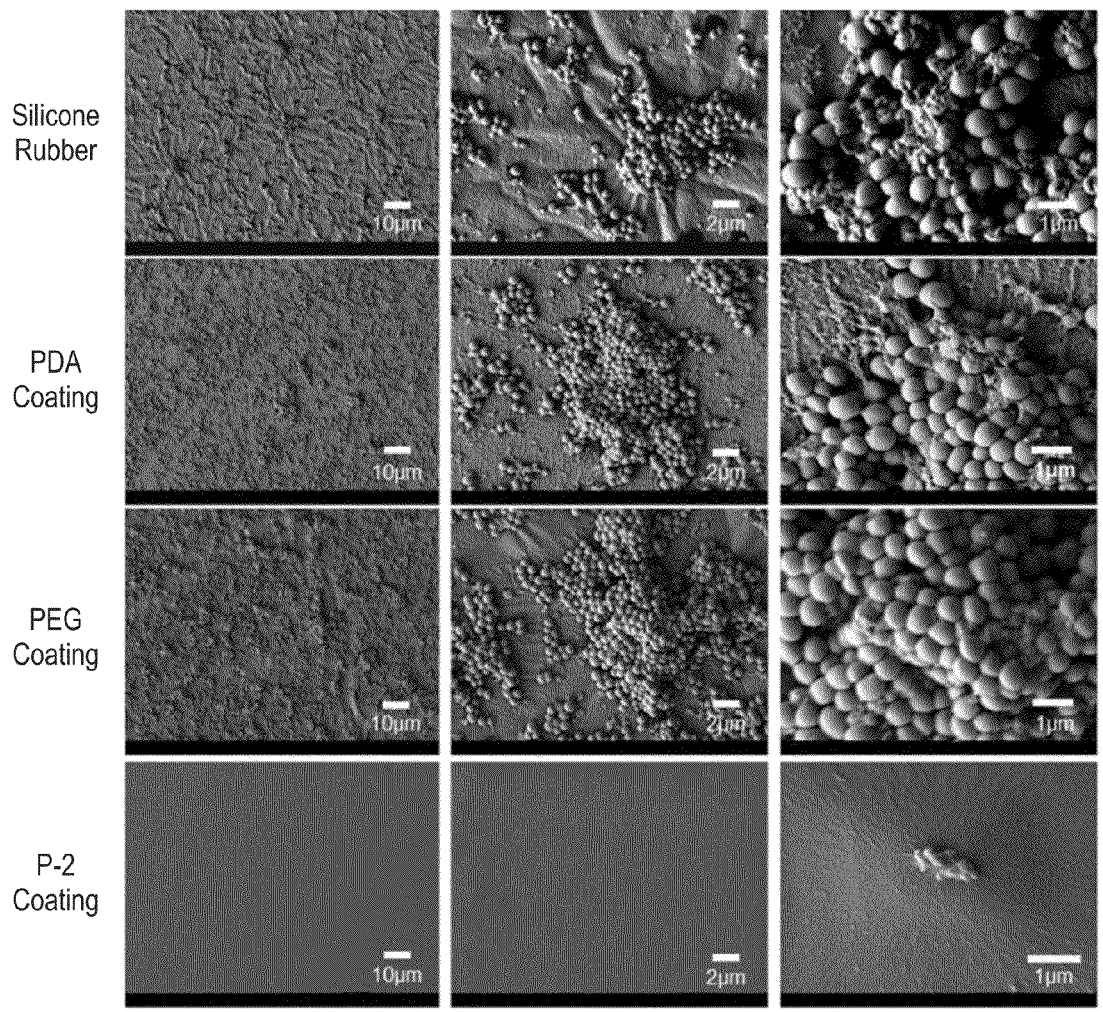
FIG. 13 is a series of scanning electron micrographs (SEM) images of the uncoated silicon rubber surface and the silicon rubber surfaces coated with dopamine (labeled "PDA Coating"), dopamine+HS-PEG-OH (labeled "PEG Coating"), and dopamine+P-2 (labeled "P-2 Coating") after 7 days incubation with *S. aureus*.

Biofilm formed on surfaces consisted of bacteria, their secretion and host polymers. Mature biofilm is observed within 7 days of exposure to *S. aureus*. Therefore, in this study, *S. aureus* biofilm was developed on the uncoated and coated silicone rubber surfaces by incubation of these surfaces with bacterial solution for 7 days. As shown in FIG. 13, a great number of bacterial cells were found on the uncoated, dopamine coated (labeled "PDA coating"), and dopamine+HS-PEG-OH coated surfaces (labeled "PEG coating") at 7 days. In sharp contrast, no bacterial cells and no trace of biofilm were found on the dopamine+P-2 coated silicone rubber surface although ruptured cell fragments were seen, suggesting that the antifouling and antimicrobial activity of the dopamine+P-2 coating can be preserved for an extended period of time.

Static Blood Compatibility

Figure 14:
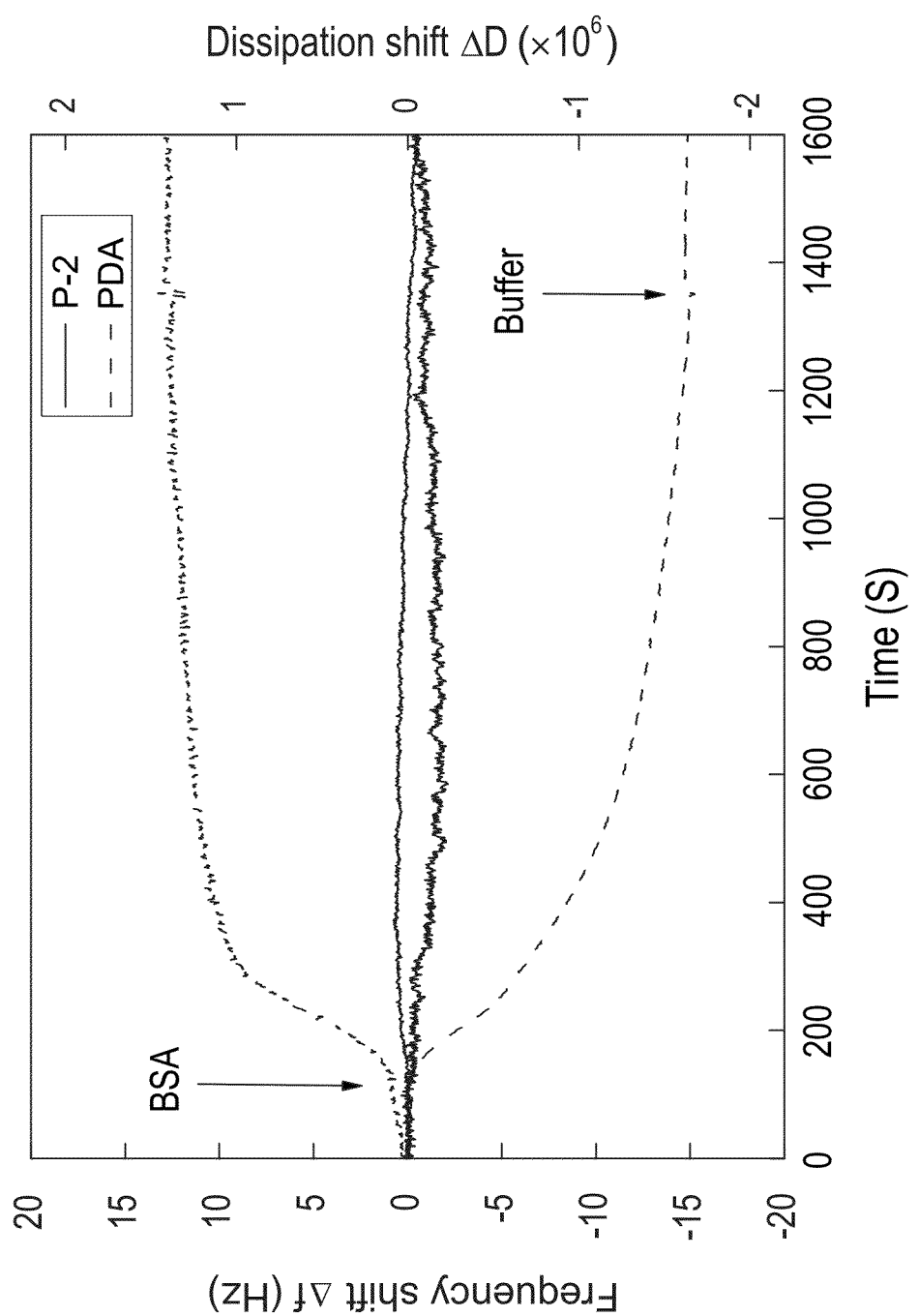
FIG. 14 is a graph showing real-time frequency shift (Δf) and dissipation shift (ΔD) of the QCM-D as a function of time of the dopamine coated (labeled "PDA") and dopamine+P-2 coated (labeled "P-2") silicon rubber in the presence of bovine serum albumin (BSA).

Blood compatibility of the coatings was evaluated via bovine serum albumin (BSA) adsorption, platelet adhesion and hemolysis analysis. When surfaces are in contact with blood, blood proteins can be adsorbed quickly, followed by platelet adhesion and activation, which can result in thrombus formation. Albumin, the most abundant protein in bloodstream, was used to study blood protein adsorption on the polymer-treated surfaces. From the real-time frequency shift ($\Delta f$) and dissipation shift ($\Delta D$) of QCM-D in FIG. 14 (graph), large $\Delta f$ and $\Delta D$ were found on the dopamine coated surface (labeled "PDA"), which indicates that BSA was easily adsorbed on the dopamine coated surface. Moreover, the frequency and dissipation values were stable after washing with phosphate buffered saline (PBS), suggesting that the BSA adsorption was stable on the dopamine coated surface. The strong interaction between BSA and dopamine coated surface is due to the reactive dopamine coating which can react with BSA amine groups. In contrast, for the dopamine+P-2 coated surface (labeled "P-2"), the small changes in $\Delta f$ and $\Delta D$ indicate that the mass and softness hardly changed when BSA was pumped over the surface, suggesting that there was no significant BSA adsorption on this surface. The prevention of protein adsorption is most likely due to the incorporation of PEG molecules in the polymer coating.

Figure 15B:
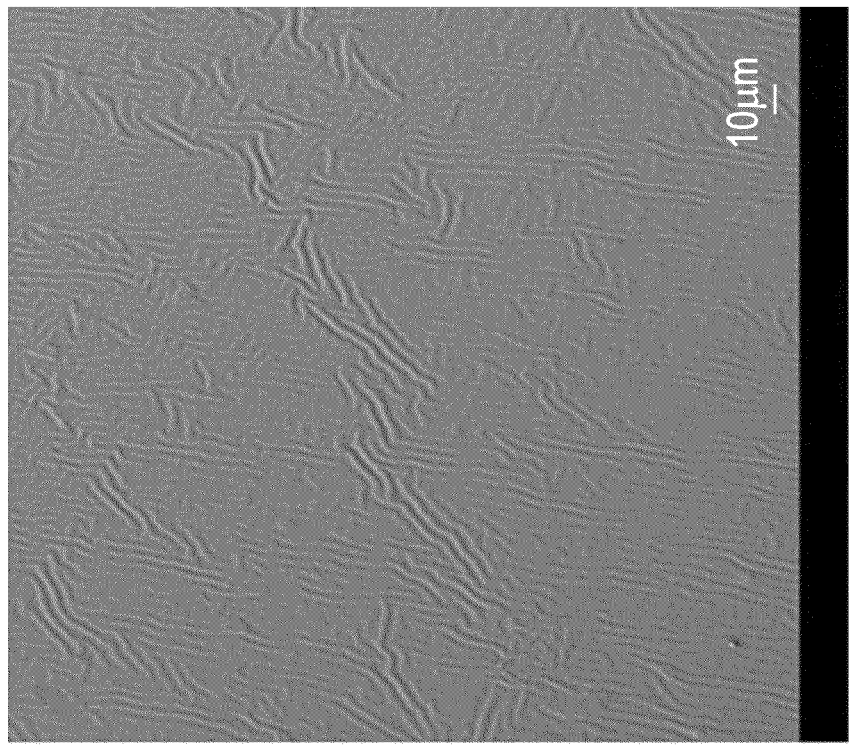
FIGS. 15A and 15B are SEM images showing blood platelets adhered on the uncoated silicone rubber surface (FIG. 15A) and the surface coated with dopamine+P-2 (FIG. 15B). The inserted image in image
Figure 15A:
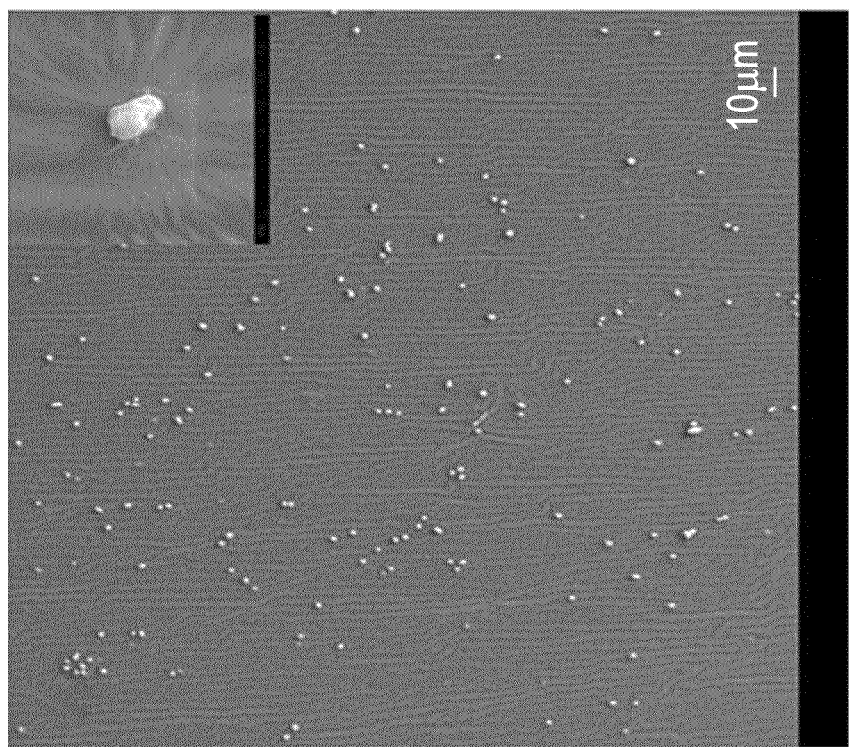

Blood platelet adhesion on the uncoated and dopamine+P-2 coated silicone rubber surfaces was examined by SEM. As shown in FIG. 15A, a large number of adhered platelets were found on the uncoated silicone rubber surface. However, on the dopamine+P-2 coated surface, no adhered platelets were observed (FIG. 15B). These results prove that the dopamine+P-2 coating was able to eliminate platelet adhesion, preventing further thrombus formation.

Figure 16:
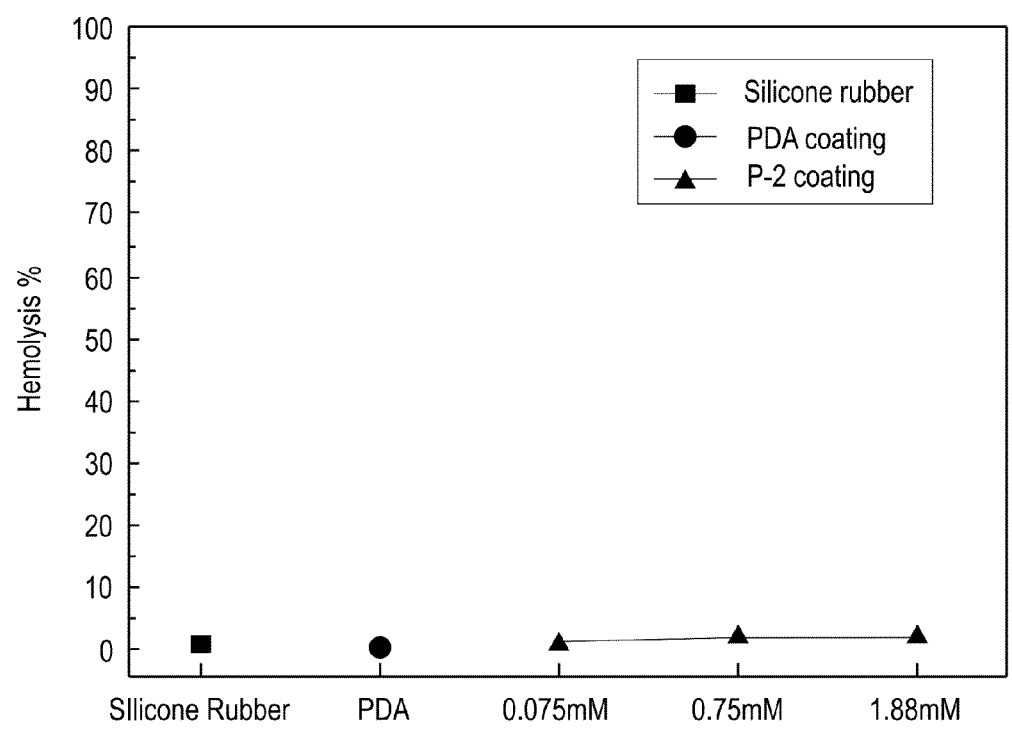
FIG. 16 is a graph showing the percent hemolysis after red blood cell contact with the uncoated silicon rubber surface and silicon rubber surfaces coated with dopamine (labeled "PDA coating") and dopamine+P-2 at various concentrations (labeled "P-2 coating").

FIG. 16 is a graph depicting the percent hemolysis after red blood cell contact with the uncoated, dopamine coated (labeled "PDA coating"), and dopamine+P-2 coated silicone rubber (labeled "P-2 coating"). Similar to the uncoated silicone rubber, the surfaces coated with dopamine and dopamine+P-2 at various concentrations did not cause significant hemolysis, which is desirable for future clinical applications.

CONCLUSION

A series of diblock copolymers of PEG and cationic polycarbonates (PEG-b-cationic polycarbonates), which are synthesized by metal-free organocatalytic ring-opening polymerization, have been successfully grafted onto silicone rubber, a commonly used catheter material, through an active polydopamine coating layer. The polymer coatings with a hydrophobic component eradicate *S. aureus* and MRSA in solution, and efficiently prevent surface fouling. In particular, the P-2 coated surfaces with the optimal polymer composition exhibit significantly higher antifouling activity than the HS-PEG-OH coated surfaces. Furthermore, the polymer coating inhibits biofilm formation without causing significant hemolysis, blood protein adsorption or platelet adhesion. Therefore, these PEG-b-cationic polycarbonates hold great potential for antifouling and antibacterial coatings for the prevention of intravascular catheter-associated infections.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. An antimicrobial silicone rubber, comprising:
   a silicone rubber substrate;
   a catechol layer bound to a surface of the silicone rubber substrate, the catechol layer comprising a catechol material, a quinone derivative thereof, and/or a polymer of any of the foregoing; and
   an antimicrobial layer disposed on the catechol layer, the antimicrobial layer comprising an antimicrobial cationic polycarbonate covalently linked to the catechol layer.

2. The antimicrobial silicone rubber of claim 1, wherein the catechol material is dopamine.

3. The antimicrobial silicone rubber of claim 1, wherein the catechol layer comprises polydopamine (PDA).

4. The antimicrobial silicone rubber of claim 1, wherein the cationic polycarbonate is a diblock copolymer comprising a poly(ethylene oxide) block and a cationic polycarbonate block.

5. The antimicrobial silicone rubber of claim 4, wherein the poly(ethylene oxide) block has a terminal sulfur group bound to the catechol layer.

6. The antimicrobial silicone rubber of claim 4, wherein the cationic polycarbonate block is a random copolymer comprising a cationic carbonate repeat unit and a hydrophobic non-charged carbonate repeat unit.

7. The antimicrobial silicone rubber of claim 1, wherein the cationic polycarbonate consists essentially of cationic carbonate repeat units comprising i) a carbonate backbone portion and ii) a side chain linked to the backbone portion, the side chain comprising a quaternary amine.

8. The antimicrobial silicone rubber of claim 1, wherein the antimicrobial silicone rubber is effective in inhibiting growth of a microbe selected from the group consisting of Gram-positive microbes, Gram-negative microbes, yeast, fungi, and combinations thereof.

9. A method, comprising:
   treating a silicone rubber substrate with a first solution comprising a first solvent and a catechol material comprising a catechol group;
   removing the first solvent, thereby forming a modified silicone rubber substrate comprising a catechol layer bound to a surface of the silicone rubber substrate, the catechol layer comprising the catechol material, a quinone derivative thereof, and/or a polymer of any of the foregoing;
   treating the modified silicone rubber substrate with a second solution comprising a second solvent and a cationic polycarbonate comprising a nucleophilic group capable of reacting with the catechol layer to form a covalent bond; and
   removing the second solvent, thereby forming an antimicrobial silicone rubber comprising an antimicrobial layer disposed on the catechol layer of the modified silicone rubber substrate, the antimicrobial layer comprising the antimicrobial cationic polycarbonate covalently bound to the catechol layer.

10. The method of claim 9, wherein the catechol material is dopamine and the catechol layer comprises polydopamine.

11. The method of claim 9, wherein the cationic polycarbonate is formed by a process comprising polymerizing a cyclic carbonate monomer by an organocatalyzed ring opening polymerization initiated by an initiator comprising an alcohol group and a thiol group.

12. The method of claim 11, wherein the initiator is HS-PEG-OH having the structure:

$$HS\diagdown\diagup\left(\diagup O\diagdown\right)_n\diagup OH,$$

wherein n is about 100 to about 150, and the cationic polycarbonate is a block copolymer.

13. The method of claim 9, wherein the cationic polycarbonate comprises a cationic repeat unit comprising a side chain quaternary amine.

14. A medical device comprising the antimicrobial silicone rubber of claim 1.

15. The medical device of claim 14, wherein the medical device is a catheter.

16. An antimicrobial medical device, comprising:
   a substrate;
   a catechol layer bound to a surface of the substrate; and
   an antimicrobial layer covalently bound to the catechol layer, wherein the antimicrobial layer is contacted by mammalian tissue and/or mammalian fluid during the intended use of the medical device;
   wherein
   the surface of the substrate comprises a material selected from the group consisting of metals, metal alloys, metal oxides, silicon oxides, semiconductors, ceramics, polymers, silicones, and combinations thereof,
   the catechol layer comprises a catechol material, a quinone derivative thereof, and/or a polymer of any of the foregoing, and
   the antimicrobial layer comprises an antimicrobial cationic polycarbonate.

17. The medical device of claim 16, wherein the catechol layer comprises polydopamine.

18. The medical device of claim 16, wherein the antimicrobial cationic polycarbonate consists essentially of cationic carbonate repeat units.

19. The medical device of claim 16, wherein the surface of the substrate comprises a silicone.

20. The medical device of claim 16, wherein the surface of the substrate comprises a metal.

* * * * *